US 6,943,158 B2
Sep. 13, 2005

(12) United States Patent
Chen et al.

(10) Patent No.: US 6,943,158 B2
(45) Date of Patent: Sep. 13, 2005

(54) DIAZINOPYRIMIDINES

(75) Inventors: Jian Jeffrey Chen, Newbury Park, CA (US); Kin-Chun Thomas Luk, North Caldwell, NJ (US)

(73) Assignees: Roche Palo Alto LLC, Palo Alto, CA (US); Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/715,666

(22) Filed: Nov. 18, 2003

(65) Prior Publication Data

US 2004/0097493 A1 May 20, 2004

Related U.S. Application Data

(60) Provisional application No. 60/427,652, filed on Nov. 18, 2002.

(51) Int. Cl.[7] ............... C07D 487/04; C07D 513/04; A61K 31/519; A61K 31/5365; A61P 9/10

(52) U.S. Cl. ............... 514/222.8; 514/229.2; 514/243; 514/234.5; 544/48; 544/66; 544/112; 544/184

(58) Field of Search ............... 544/48, 66, 112, 544/184; 514/222.8, 229.2, 234.5, 243

(56) References Cited

U.S. PATENT DOCUMENTS 4,025,510 A * 5/1977 Elliott .................. 544/9

FOREIGN PATENT DOCUMENTS

| GB | 1353534 | 5/1974 |
|---|---|---|
| JP | 53028-192 | 3/1978 |
| WO | WO 02/18380 A1 | 3/2002 |
| WO | WO 03/055883 A1 | 7/2003 |

OTHER PUBLICATIONS

Elliot et al. {J. Heterocyclic Chem, (1981), pp 799–800, vol. 189, No. 4}.*
Elliot et al. {Journal of Organic Chemistry (1980), 45(18), 3677–81}.*
Bioorg. Med Chem. Lett. 14(2004) 5383–7.*
Elliott, A. J., et al., "Hydrazides and Thiohydrazides as Sources of Condensed Oxadiazine and Thiadiazines, Including Novel Azo Derivatives Based on Dithizone", J. Org. Chem. (1980), pp. 3677–3681, vol. 45, No. 18.
Elliott, A. J., et al., "Reactions of Benzothiohydrazide as a Bidentate Nucleophile", J. Heterocyclic Chem, (1981), pp. 799–800, vol. 189, No. 4.
Guertin, K. R., et al., "Identification of a Novel Class of Orally Active Pyrimido[5,4-3][1,2,4]triazine-5,7-diamine-Based Hypoglycemic Agents with Protein Tyrosine Phosphatase Inhibitory Activity", Bioorganic & Medicinal Chemistry Letters (2003) pp. 2895–2898, vol. 13, No. 17.

Al–Hassan, et al., "Specific enzyme inhibitors in vitamin biosynthesis," J. Chemical Res., Synop., (1980), pp 278–279, vol. 9.
Brown, DJ; et al., "Aza–analogs of pteridine. VI. 3–Alkyl-5(and 7)-aminopyrimido[5,4-e] astriazines and related compounds," J. Chemical Society, (1972), pp 2316–19, vol. 18.
Yoneda, et al., "6–Azapurines (imidazol[4,5-e]-as-triazines)," J. Chemical Society: Chemical Commun., (1976), pp 658–659, vol. 16.
Yoshinari et al., "Effects of a dual inhibitor of tumor necrosis factor–alpha and interleukin–1 on lipopolysaccharide–induced lung injury in rats: Involvement of the p38 mitogen–activated protein kinase pathway," Critical Care Med (2001) pp 628–634, vol. 29:3.
Bhatia et al., "Role of inflammatory mediators in the pathophysiology of acute respiratory distress syndrome" Journal of Pathology (2004) pp 145–156, vol. 202.
Aringer et al., "Safety and Efficacy of Tumor Necrosis Factor Alpha Blockade in Systemic Lupus Erythematosus" Arthitis & Rheumatism (Oct. 2004) pp 3161–3169, vol. 50:10.

(Continued)

Primary Examiner—Mark L. Berch
Assistant Examiner—Kahsay Habte
(74) Attorney, Agent, or Firm—Grant D. Green

(57) ABSTRACT

Compounds of formula I are p38 inhibitors:

I or a pharmaceutically acceptable salt thereof,
wherein
$R^1$ is hydrogen or alkyl;
$R^2$ alkyl, haloalkyl, aryl, aralkyl, heteroaryl, heteroaralkyl, cycloalkyl, cycloalkylalkyl, heteroalkyl-substituted cycloalkyl, heterosubstituted cycloalkyl, heteroalkyl, cyanoalkyl, heterocyclyl, heterocyclylalkyl, or —$Y^1$—C(O)—$Y^2$—$R^{11}$ (where $Y^1$ and $Y^2$ are independently either absent or an alkylene group and $R^{11}$ is hydrogen, alkyl, haloalkyl, hydroxy, alkoxy, amino, monoalkylamino or dialkylamino);
$R^3$ is hydrogen, alkyl, cycloalkyl, cycloalkylalkyl, heterosubstituted cycloalkyl, heterocyclyl, aryl, aralkyl, haloalkyl, heteroalkyl, cyanoalkyl, -alkylene-C(=O)—$R^4$ (where $R^4$ is hydrogen, alkyl, hydroxy, alkoxy, amino, monoalkylamino or dialkylamino), or acyl;
$Ar^1$ is aryl;
$X^1$ is O, $NR^5$ or S, where $R^5$ is hydrogen or alkyl; and
$X^2$ is a bond, O, $NR^6$, S or $CH_2$, where $R^6$ is hydrogen or alkyl.

30 Claims, No Drawings

OTHER PUBLICATIONS

Goldring et al., "The Role of Cytokines in Cartilage Matrix Degeneration in Osteorathritis" Clinical Orthopaedics and Related Research (2004) pp S27–S36, No. 427S.

Di Giovine et al., "Urate Crystals Stimulate Production of Tumor Necrosis Factor Alpha from Human Blood Monocytes and Synovial Cells" Journal of Clin. Invest. (Apr. 1991) pp 1375–1381, vol. 87.

Muller, Thomas. "CPI–1189 Centaur" Current Opinion in Investigational Drugs (2002) pp 1763–1767, vol. 3:12.

* cited by examiner

DIAZINOPYRIMIDINES

RELATED APPLICATIONS

This application claims priority from U.S. Ser. No. 60/427,652, filed 18 Nov. 2002, incorporated herein by reference in its entirety.

FIELD OF THE INVENTION

The present invention relates to diazinopyrimidines, a process for their manufacture, compositions comprising the same, and methods for using the same. In particular, the present invention relates to pyrimido[4,5-e]oxadiazines.

BACKGROUND OF THE INVENTION

Protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

Tyrosine kinases are a subset of protein kinases that catalyze the transfer of the terminal phosphate of adenosine triphosphate to tyrosine residues on protein substrates. These kinases play an important part in the propagation of growth factor signal transduction that leads to cellular proliferation, differentiation and migration.

For example, fibroblast growth factor (FGF) and vascular endothelial growth factor (VEGF) have been recognized as important mediators of tumor promoted angiogenesis. VEGF activates endothelial cells by signaling through two high affinity receptors, one of which is the kinase insert domain-containing receptor (KDR). See Hennequin L. F. et. al., *J. Med. Chem.*, 2002, 45, 1300. FGF activates endothelial cells by signaling through the FGF receptor (FGFR). Solid tumors depend upon the formation of new blood vessels (angiogenesis) to grow. Accordingly, inhibitors of the receptors FGFR and KDR that interfere with the growth signal transduction, and thus slow down or prevent angiogenisis, are useful agents in the prevention and treatment of solid tumors. See Klohs W. E. et. al., *Current Opinion in Biotechnology*, 1999, 10, 544.

Other protein kinases include mitogen-activated protein kinases (MAP) which is a family of proline-directed serine/threonine kinases that activate their substrates by dual phosphorylation. One group of MAP kinases is the p38 kinase group which includes various isoforms (e.g., p38α, p39β, p38γ and p38δ). The p38 kinases are responsible for phosphorylating and activating transcription factors as well as other kinases, and are themselves activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

Additionally, the involvement of p38 has been implicated in stroke, Alzheimer's disease, osteoarthritis, lung injury, septic shock, angiogenesis, dermatitis, psoriasis and atopic dermatitis. *J. Exp. Opin. Ther. Patents*, (2000) 10(1).

The inhibition of these cytokines by inhibition of the p38 kinase is of benefit in controlling, reducing and alleviating many of these disease states.

There are several examples of synthetic inhibitors for various protein kinases. Typically, kinase inhibitors block the phosphorylation of substrates by tightly interacting with the protein kinase ATP binding site (or "active site"). See WO 98/24432 and Hennequin L. F. et. al., *J. Med. Chem.*, 2002, 45, 1300. Several of these compounds inhibit multiple targets. See also, PCT Publication Nos. WO 99/61444, WO 02/18380, and WO 01/64679; and U.S. Pat. No. 6,150,373;

However, there continues to be a need for compounds that are effective in inhibiting the catalytic activity of protein kinases, in particular FGF and KDR kinases for treating one or more types of solid tumors. It is particularly desirable to provide inhibitors that are selective for FGF and KDR. Selectivity is particularly desired due to a potential concomitant toxicity and other undesirable complications that may follow from inhibiting multiple targets. It is preferable that such inhibitors also possess advantageous bioavailability profiles.

SUMMARY OF THE INVENTION

In one aspect of the present invention provides compounds represented by the formula:

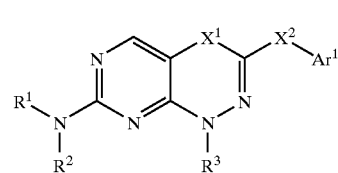

I or a pharmaceutically acceptable salt thereof,
wherein
  $R^1$ is hydrogen or alkyl;
  $R^2$ is alkyl, haloalkyl, aryl, aralkyl, heteroaryl, heteroaralkyl, cycloalkyl, cycloalkylalkyl, heteroalkyl-substituted cycloalkyl, heterosubstituted cycloalkyl, heteroalkyl, cyanoalkyl, heterocyclyl, heterocyclylalkyl, or —$Y^1$—C(O)—$Y^2$—$R^{11}$ (where $Y^1$ and $Y^2$ are independently either absent or an alkylene group and $R^{11}$ is hydrogen, alkyl, haloalkyl, hydroxy, alkoxy, amino, monoalkylamino or dialkylamino);

$R^3$ is hydrogen, alkyl, cycloalkyl, cycloalkylalkyl, heterosubstituted cycloalkyl, heterocyclyl, aryl, aralkyl, haloalkyl, heteroalkyl, cyanoalkyl, -alkylene-C(=O)—$R^4$ (where $R^4$ is hydrogen, alkyl, hydroxy, alkoxy, amino, monoalkylamino or dialkylamino), or acyl;

$Ar^1$ is aryl;

$X^1$ is O, $NR^5$, or S, where $R^5$ is hydrogen or alkyl; and $X^2$ is a bond, O, $NR^6$, S or $CH_2$, where $R^6$ is hydrogen or alkyl.

The compounds of formula I and their aforementioned salts are inhibitors of protein kinases, and exhibit effective activity against p38 MAP kinase and FGFR kinase. Therefore, the compounds can be used for the treatment of diseases mediated by the pro-inflammatory cytokines such as TNF and IL-1 as well as proliferative disorders such as cancer and restonosis.

Thus, in another aspect, the present invention relates to methods for the treatment of p38 MAP kinase and FGFR kinase mediated diseases or conditions in which a therapeutically effective amount of a compound of formula I is administered to a patient in need of such treatment.

In yet another aspect, the present invention relates to methods for preparing the compounds described above.

In yet still another aspect, the present invention relates to methods for preparing medicaments useful for the treatment of the p38 MAP kinase and FGFR kinase mediated diseases and conditions.

DETAILED DESCRIPTION OF THE INVENTION

Definitions

"Acyl" means a moiety —C(O)R, where R is hydrogen, alkyl, cycloalkyl, cycloalkylalkyl, haloalkyl, aryl, aralkyl, heteroaryl, or heteroaralkyl.

"Acylamino" means a moiety —NR'C(O)R, where R' is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethylcarbonylamino, benzoylamino, benzylcarbonylamino, and the like.

"Alkoxy" means a moiety —OR where R is an alkyl as defined herein e.g., methoxy, ethoxy, propoxy, butoxy and the like.

"Alkyl" means a linear saturated monovalent hydrocarbon moiety of one to six carbon atoms or a branched saturated monovalent hydrocarbon moiety of three to six carbon atoms, e.g., methyl, ethyl, propyl, 2-propyl, n-butyl, iso-butyl, tert-butyl, pentyl, and the like.

"Alkylthio" means a group —SR where R is alkyl, e.g. methylthio, ethylthio, butylthio and the like.

"Alkylsulfonyl" means a moiety of the formula —S(=O)$_2$R, where R is alkyl. Exemplary alkylsulfonyl groups include methylsulfonyl, ethylsulfonyl, and the like.

"Alkoxycarbonyl" means a moiety of the formula —COOR, where R is alkyl. Exemples include methoxycarbonyl, ethoxycarbonyl, and the like.

"Alkylsulfonyloxy" means a moiety of the formula —OS(O)$_2$R, where R is alkyl.

"Carbamoyl", "N-alkyl-carbamoyl" and "N,N-dialkylcarbamoyl" means a moiety —O—C(=O)—NR$_2$ where both R are hydrogen, one of R is hydrogen and the other is alkyl, and both R are independently the same or different alkyl, respectively.

"Carboxamido", "N-monoalkylcarboxamido", and "N-dialkylcarboxamido" means a moiety of the formula —CONR$_2$, where both R are hydrogen, one R is hydrogen and the other is alkyl, and both R are independently the same or different alkyl, respectively.

"O—N-alkylcarbamate" refers to a moiety of the formula —OC(=O)NHR, where R is alkyl.

"Alkylene" means a linear saturated divalent hydrocarbon moiety of one to six carbon atoms or a branched saturated divalent hydrocarbon moiety of three to six carbon atoms, e.g., methylene, ethylene, 2,2-dimethylethylene, propylene, 2-methylpropylene, butylene, pentylene, and the like.

"Aryl" means a monovalent monocyclic or bicyclic aromatic hydrocarbon ring which is optionally substituted independently with one or more substituents, preferably one, two or three, substituents preferably selected from the group consisting of alkyl, hydroxy, alkoxy, alkoxycarbonyl, carboxamido, N-monoalkylcarboxamido, N-dialkylcarboxamido, alkylsulfonyloxy, carbamoyl, N-alkylcarbamoyl, N,N-dialkylcarbamoyl, heterocyclyl, cycloalkyl, haloalkyl, haloalkoxy, heteroalkyl, halo, nitro, cyano, amino, monoalkylamino, dialkylamino, methylenedioxy, ethylenedioxy and acyl. More specifically the term aryl includes, but is not limited to, phenyl, chlorophenyl, methoxyphenyl, 1-naphthyl, 2-naphthyl, and the derivatives thereof.

"Cyanoalkyl" refers to an alkyl group, as defined herein, which is substituted with a cyano group.

"Cycloalkyl" refers to a saturated monovalent cyclic hydrocarbon moiety of three to seven ring carbons e.g., cyclopropyl, cyclobutyl, cyclohexyl, 4-methyl-cyclohexyl, and the like.

"Cycloalkylalkyl" means a moiety —$R^aR^b$ where $R^a$ is an alkylene group and $R^b$ is cycloalkyl group as defined herein, e.g., cyclohexylmethyl, and the like.

"Dialkylamino" means a moiety —NRR' where R and R' independently represent an alkyl, hydroxyalkyl, cycloalkyl, or cycloalkylalkyl group as defined herein or R and R' together form an alkylene group. Representative examples include, but are not limited to dimethylamino, methylethylamino, di(1-methylethyl)amino, (methyl) (hydroxyethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl) (ethyl)amino 3-piperidinyl-propyl, and the like.

The terms "halo", "halide", and "halogen" are used interchangeably herein and refer to fluoro, chloro, bromo, or iodo, preferably fluoro and chloro.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroalkyl" means an alkyl moiety as defined herein wherein one, two or three hydrogen atoms have been replaced with a substituent independently selected from the group consisting —$OR^a$, —$NR^bR^c$, and —$S(O)_nR^d$ (where n is an integer from 0 to 2), with the understanding that the point of attachment of the heteroalkyl moiety is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroalkylsubstituted cycloalkyl" means a cycloalkyl moiety as defined herein wherein one, two or three hydrogen atoms in the cycloalkyl moiety have been replaced with a heteroalkyl group with the understanding that the heteroalkyl moiety is attached to the cycloalkyl moiety via a carbon-carbon bond. Representative examples include, but are not limited to, 1-hydroxymethylcyclopentyl, 2-hydroxymethylcyclohexyl, and the like.

"Heterosubstituted cycloalkyl" means a cycloalkyl moiety as defined herein wherein one, two or three hydrogen atoms in the cycloalkyl moiety have been replaced with a substituent independently selected from the group consisting of hydroxy, alkoxy, amino, acylamino, monoalkylamino, dialkylamino, oxo (C=O), imino, hydroximino (=NOH), $NR'SO_2R^d$ (where R' is hydrogen or alkyl and $R^d$ is alkyl, cycloalkyl, amino, monoalkylamino or dialkylamino), —X—C(O)R (where X is O or NR', R is hydrogen, alkyl, haloalkyl, alkoxy, amino, monoalkylamino, dialkylamino, or optionally substituted phenyl, and R' is H or alkyl), or —S(O)$_n$R (where n is an integer from 0 to 2) such that when n is 0, R is hydrogen, alkyl, cycloalkyl, or cycloalkylalkyl, and when n is 1 or 2, R is alkyl, cycloalkyl, cycloalkylalkyl, amino, acylamino, monoalkylamino or dialkylamino. Representative examples include, but are not limited to, 2-, 3-, or 4-hydroxycyclohexyl, 2-, 3-, or 4-aminocyclohexyl, 2-, 3-, or 4-methanesulfonamido-cyclohexyl, and the like, preferably 4-hydroxycyclohexyl, 2-aminocyclohexyl or 4-methanesulfonamido-cyclohexyl.

"Heterocyclyl" means a saturated or unsaturated non-aromatic cyclic moiety of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclyl may be optionally substituted independently with one, two, or three substituents selected from alkyl, haloalkyl, heteroalkyl, halo, nitro, cyano, cyanoalkyl, hydroxy, alkoxy, amino, monoalkylamino, dialkylamino, aralkyl, —(X)$_n$—C(O)R (where X is O or NR', n is 0 or 1, R is hydrogen, alkyl, haloalkyl, hydroxy (when n is 0), alkoxy, amino, monoalkylamino, dialkylamino, or optionally substituted phenyl, and R' is H or alkyl), -alkylene-C(O)R (where R is OR or NR'R" and R is hydrogen, alkyl or haloalkyl, and R' and R" are independently hydrogen or alkyl), or —S(O)$_n$R (where n is an integer from 0 to 2) such that when n is 0, R is hydrogen, alkyl, cycloalkyl, or cycloalkylalkyl, and when n is 1 or 2, R is alkyl, cycloalkyl, cycloalkylalkyl, amino, acylamino, monoalkylamino or dialkylamino. More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, N-methanesulfonyl-piperidin-4-yl, and the derivatives thereof.

"Heterocyclylalkyl" means a moiety —$R^aR^b$ where $R^a$ is an alkylene group and $R^b$ is a heterocyclyl group as defined herein.

"Hydroxyalkyl" means a subset of heteroalkyl moiety as defined herein which is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Monoalkylamino" means a moiety —NHR where R is an alkyl, hydroxyalkyl, cycloalkyl, or cycloalkylalkyl group as defined above, e.g., methylamino, (1-methylethyl)amino, hydroxyethylamino, cyclohexylamino, cyclohexylmethylamino, cyclohexylethylamino, and the like.

"Optionally substituted phenyl" means a phenyl ring which is optionally substituted independently with one or more substituents, preferably one or two substituents selected from the group consisting of alkyl, hydroxy, alkoxy, alkoxycarbonyl, carboxamido, N-monoalkylcarboxamido, N-dialkylcarboxamido, alkylsulfonyloxy, carbamoyl, N-alkylcarbamoyl, N,N-dialkylcarbamoyl, heterocyclyl, cycloalkyl, haloalkyl, haloalkoxy, heteroalkyl, heterocyclyl, cycloalkyl, monoalkylamino, dialkylamino, halo, nitro, cyano, amino, methylenedioxy, ethylenedioxy, and acyl.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, or sulfhydryl group, respectively. Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1–92, Elesevier, New York-Oxford (1985).

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, 2$^{nd}$ ed. 1991) and Harrison and Harrison et al., *Compendium of Synthetic Organic Methods*, Vols. 1–8 (John Wiley and Sons, 1971–1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitroveratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

In reference to a chemical reaction, the terms "treating", "contacting" or "reacting" are used interchangeably herein and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Abbreviations

The abbreviations used herein are as follows:

MCPBA: m-chloroperbenzoic acid or 3-chloroperbenzoic acid.

NMP: N-methylpyrrolidine.

THF: tetrahydrofuran.

DMF: dimethylformamide.

TLC: thin layer chromatography.

EtOAc: ethyl acetate.

Compounds of the Present Invention

In one aspect, the present invention provides a compound of the formula:

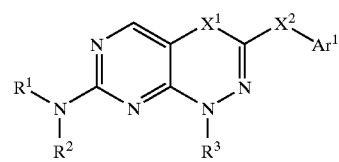

I or a pharmaceutically acceptable salt thereof, where $R^1$, $R^2$, $R^3$, $X^1$, $X^2$, and $Ar^1$ are as defined i Summary of the Invention above.

With respect to Compound of Formula I above:

Preferably, $R^1$ is hydrogen.

Preferably, $R^2$ is heteroalkyl, cycloalkyl, heterocyclyl, heterosubstituted cycloalkyl, heteroaryl or an aryl. More preferably, $R^2$ is heteroalkyl, aryl or heterocyclyl. In one embodiment, $R^2$ is optionally substituted phenyl. Still more preferably, $R^2$ is heterocyclylphenyl, alkylthiophenyl, alkylsulfinylphenyl, alkylsulfonylphenyl, phenyl, halophenyl, hydroxyphenyl, acylphenyl, cyanophenyl, alkoxycarbonylphenyl, carboxamidophenyl, N-alkylcarboxamidophenyl, N,N-dialkylcarboxamidophenyl, alkylsulfonyloxyphenyl, carbamoylphenyl, N-alkylcarbamoylphenyl, and N,N-dialkylcarbamoylphenyl. Examples include 4-morpholinophenyl, 3-methylthiophenyl, 3-methylsulfinylphenyl, 3-methylsulfonylphenyl, phenyl, 4-fluorophenyl, 3-chlorophenyl, 3-acetylphenyl, 3-cyanophenyl, 3-methoxycarbonyl-phenyl, 3-amidophenyl, 3-methylsulfonyloxy-pheny 3-(methylamido)phenyl, and 3-N-methylcarbamoylphenyl. In yet another embodiment, $R^2$ is:

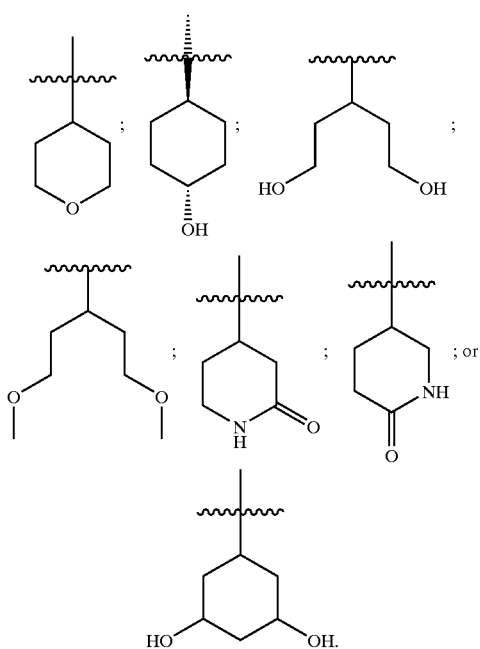

Preferably, $R^3$ is hydrogen, alkyl, aryl, cycloalkyl, heterocyclyl, heterosubstituted cycloalkyl or heteroalkyl.

More preferably, $R^3$ is methyl, heteroalkyl (e.g. 1-methylhydroxypropyl or 2-dimethylaminoethyl), heterosubstituted cycloalkyl (e.g. 3-methoxy-cyclopentyl) or heterocyclyl.

Preferably, $X^1$ is preferably $CH_2$ or O. More preferably $X^1$ is O.

Preferably, $X^2$ is a bond, $NR^6$ or $CH_2$, where $R^6$ is hydrogen or alkyl. More preferably, $X^2$ is a bond.

Preferably, $Ar^1$ is a phenyl that is optionally substituted independently with one or more of halogen, alkyl (preferably methyl), trifluoromethyl, alkoxy (preferably methoxy), trifluoromethoxy, cyano, nitro, amino or dialkylamino (preferably dimethylamino). In certain embodiments, $Ar^1$ is 2-halophenyl, 4-halophenyl, 2,4-dihalophenyl, 2,6-dihalophenyl, 2-alkylphenyl (preferably 2-methylphenyl), 1-alkoxyphenyl, 2-alkoxyphenyl, 4-alkoxyphenyl, 3,5-dialkoxyphenyl, 2-halo-5-alkoxyphenyl or 2-dialkylamino-6-fluorophenyl. In another embodiment $Ar^1$ is 2,6-dichlorophenyl.

Still further, combinations of the preferred groups described herein will form other preferred embodiments. For example, in one particularly preferred embodiment $R^1$ is hydrogen, $R^2$ is heteroalkyl, heterocyclyl or alkyl, $R^3$ is alkyl, aryl, and heterocyclyl, $X^1$ is O, $X^2$ is a bond, and $Ar^1$ is an optionally substituted phenyl. In this manner, a variety of preferred compounds are embodied within the present invention.

Some of the representative Compounds of Formula I are shown in Table 1 below:

TABLE 1

Representative Compounds of Formula I:

| Cpd. No. | Structure | M. Pt. °C. | MS (M + H) | Example |
|---|---|---|---|---|
| 1 | 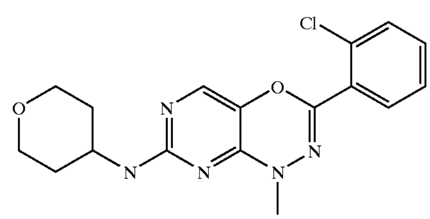 | 171.0–172.1 | 360.2 | 1 |
| 2 | 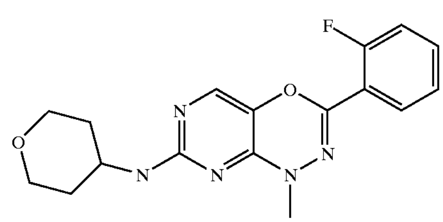 | | 344.2 | |
| 3 | 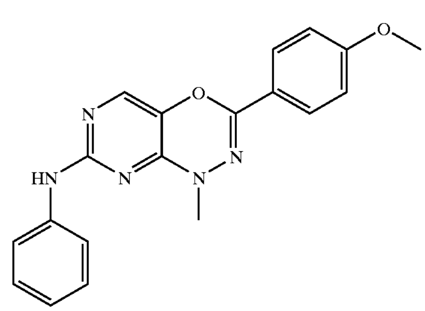 | | 348.1458 | 6 |

TABLE 1-continued
Representative Compounds of Formula I:
| Cpd. No. | Structure | M. Pt. °C. | MS (M + H) | Example |
|---|---|---|---|---|
| 4 | 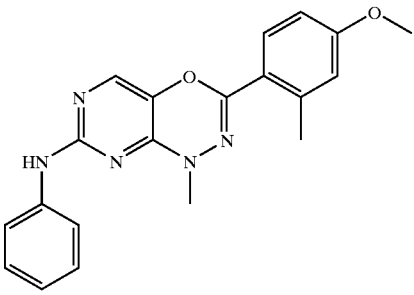 | | 362.1614 | 10 |
| 5 | 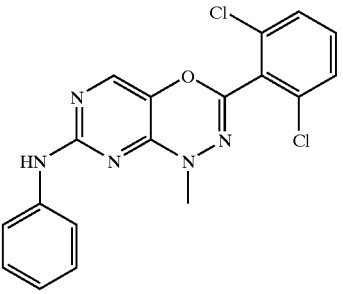 | | 386.0574 | 14 |
| 6 | 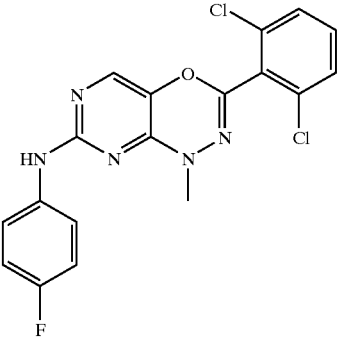 | | 404.0482 | 15 |
| 7 | 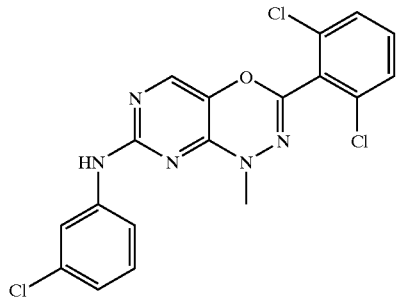 | | 420.0183 | 16 |

TABLE 1-continued
Representative Compounds of Formula I:
| Cpd. No. | Structure | M. Pt. °C. | MS (M + H) | Example |
|---|---|---|---|---|
| 8 | 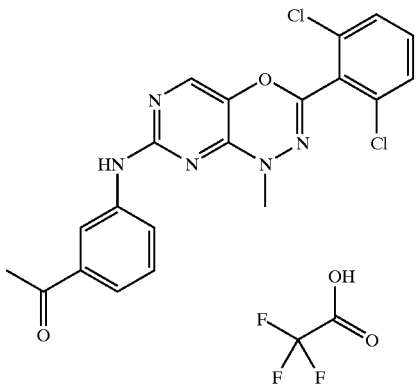 | | 428.0676 | 17 |
| 9 | 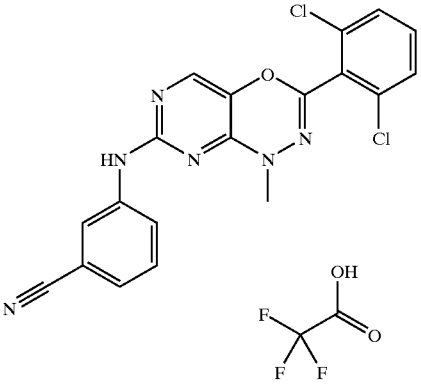 | | 411.0524 | 18 |
| 10 | 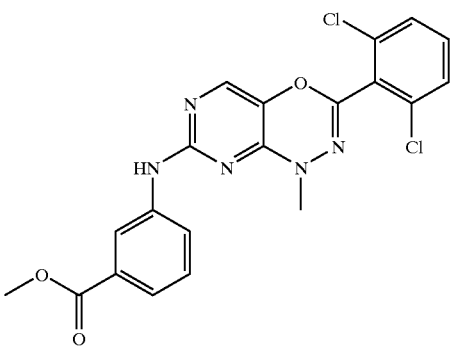 | | 444.0628 | 19 |
| 11 | 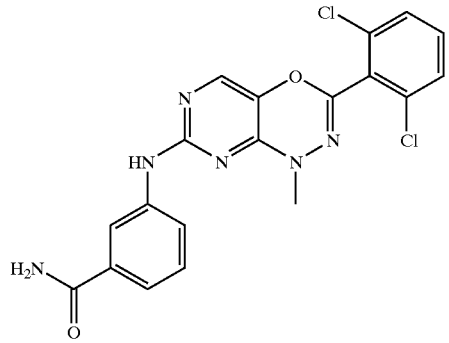 | | 429.0632 | 20 |

TABLE 1-continued

Representative Compounds of Formula I:

| Cpd. No. | Structure | M. Pt. ° C. | MS (M + H) | Example |
|---|---|---|---|---|
| 12 | 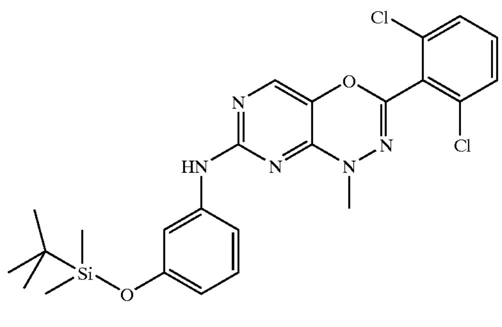 | | | 22 |
| 13 | 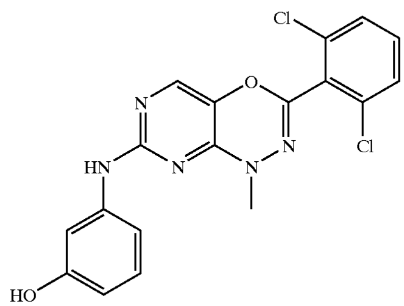 | | 402.0523 | 23 |
| 14 | 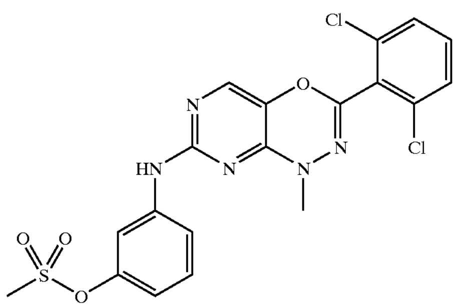 | | 480.0300 | 24 |
| 15 | 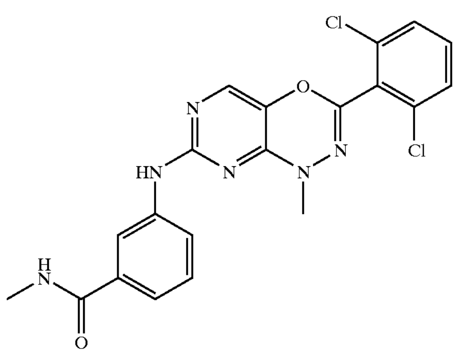 | | 443.0791 | 25 |

TABLE 1-continued

Representative Compounds of Formula I:

| Cpd. No. | Structure | M. Pt. °C. | MS (M + H) | Example |
|---|---|---|---|---|
| 16 | 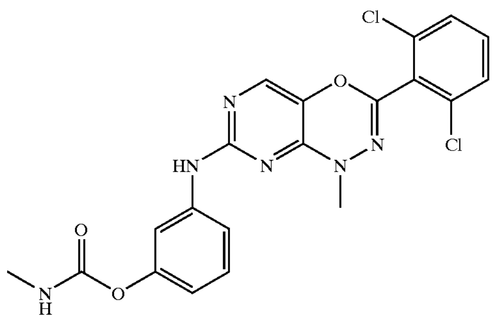 | | 459.0740 | 26 |
| 17 | 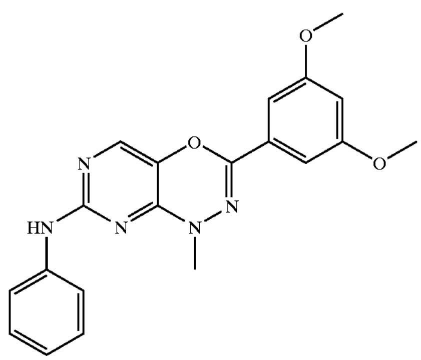 | | 378.1566 | 30 |
| 18 | 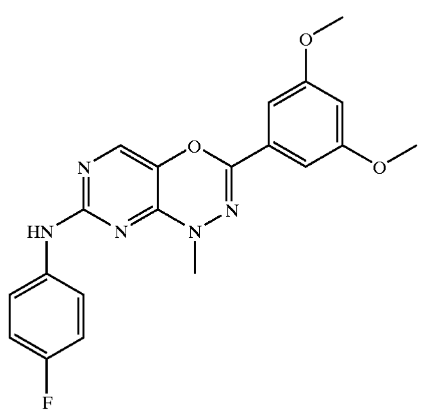 | | 396.1471 | 31 |
| 19 | 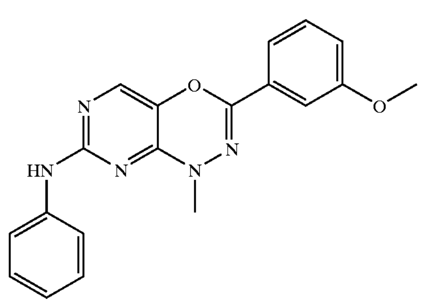 | | 348.1459 | 35 |

TABLE 1-continued

Representative Compounds of Formula I:

| Cpd. No. | Structure | M. Pt. ° C. | MS (M + H) | Example |
|---|---|---|---|---|
| 20 | 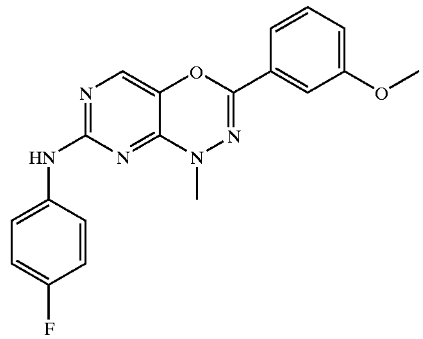 | | 366.1365 | 36 |
| 21 | 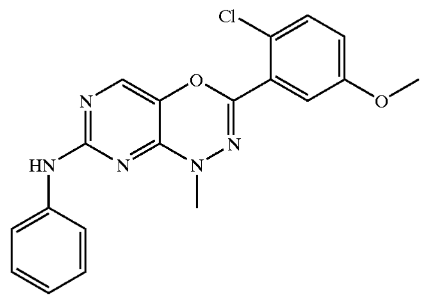 | | 382.1072 | 40 |
| 22 | 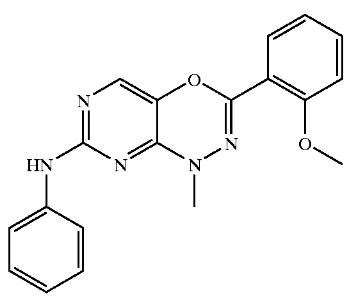 | | 348.1458 | 44 |
| 23 | 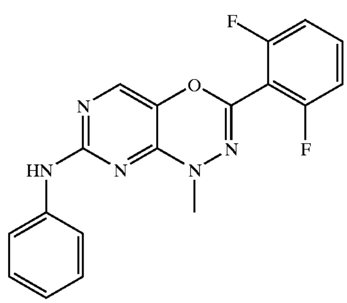 | | 353.1088 | 48 |
| 24 | 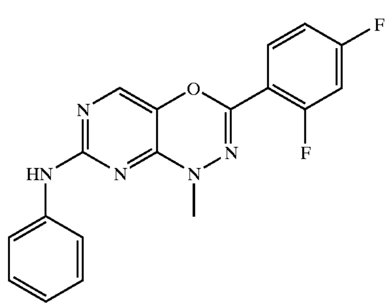 | | 353.1092 | 52 |

TABLE 1-continued

Representative Compounds of Formula I:

| Cpd. No. | Structure | M. Pt. ° C. | MS (M + H) | Example |
|---|---|---|---|---|
| 25 | 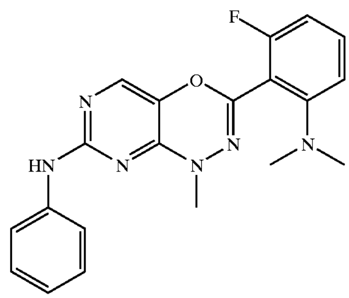 | | | 55 |
| 26 | 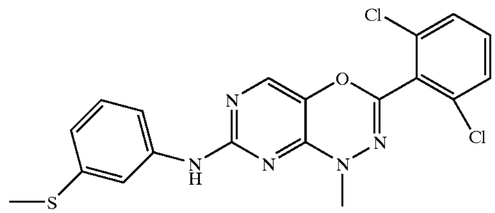 | | | 2 |
| 27 | 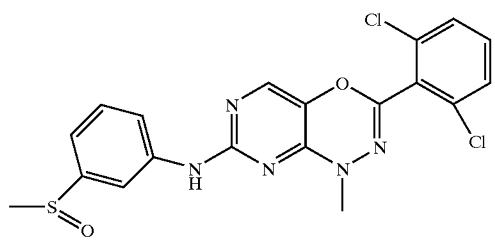 | | | 2 |
| 28 | 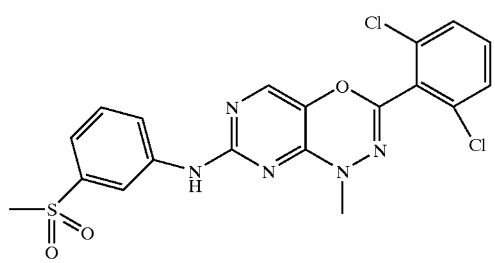 | | | 2 |
| 29 | 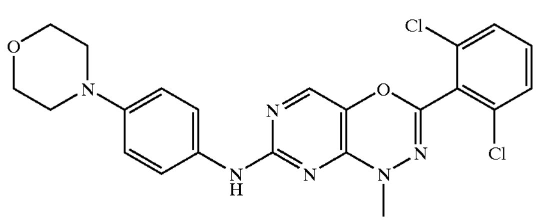 | 192.2–200.3 | 471 | 64 |
| 30 | 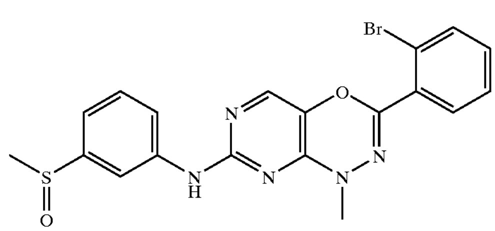 | | 460 | 62 |

TABLE 1-continued

Representative Compounds of Formula I:

| Cpd. No. | Structure | M. Pt. ° C. | MS (M + H) | Example |
|---|---|---|---|---|
| 31 | 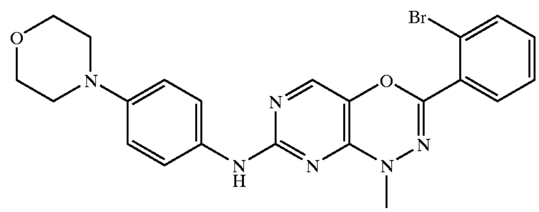 | | 482 | 63 |

Additional examples of groups corresponding to $R^1$, $R^2$ and $R^3$ may be found in U.S. patent application Ser. No. 10/073,845, filed 11 Feb. 2002, published as US 2003-0171584, which is incorporated herein by reference in its entirety with $R^1$ and $R^2$ in the present invention corresponding to $R^2$ and $R^1$ in U.S. Ser. No. 10/073,845. Additional examples of groups corresponding to $R^1$ and $R^2$ can also be found in U.S. Ser. No. 09/693,337, filed 20 Oct. 2000, now U.S. Pat. No. 6,451,804 and U.S. Ser. No. 09/943,407 filed 30 Aug. 2001, now U.S. Pat. No. 6,506,749, both of which are incorporated herein by reference in their entirety. These examples include, without limitation, 3-hydroxy-2-methylprop-2-yl, 3-hydroxyprop-2-yl, 2-hydroxypropyl, 2,3-dihydroxypropyl, 2,4-dihydroxybutyl, 2-carboxy-1-methylethyl, 1-hydroxybut-2-yl, 1,3-dihydroxyprop-2-yl, 1-hydroxymethyl-cyclopent-1-yl, 1-hydroxymethyl-cyclohex-1-yl, 4-hydroxycyclohexyl, 4-methoxycyclohexyl, 4-(2-methoxyethyl)-cyclohexyl, 4-hydroxy-cyclohexylmethyl, 4-(2,3-dihydroxypropoxy)-cyclohexyl, 4-acetoxy-cyclohexyl, 4-carbamoyloxy-cyclohexyl, 4-(N-methyl)carbamoyloxy-cyclohexyl, 4-allyloxy-cyclohexyl, 4-methoxycarbonyloxy-cyclohexyl, benzyl, 4-oxo-cyclohexyl, 1,4-dioxaspiro[4.5]dec-8-yl, 3-hydroxymethyl-3-methyl-1,5-dioxaspiro[5.5]undec-7-yl, 2,4-dioxo-1,3-diazaspiro[4.5]dec-8-yl, 4-hydroximino-cyclohexyl, 4-aminocyclohexyl, 4-methanesulfonylamino-cyclohexyl, 4-N,N-dimethylsulfamylamino-cyclohexyl, piperidin-4-yl, N-benzylpiperidin-4-yl, N-(2-hydroxyethyl)-piperidin-4-yl, N-(2,3-dihydroxypropyl)-piperidin-4-yl, N-(2-cyanoethyl)-piperidin-4-yl, N-(cyanomethyl)-piperidin-4-yl, 4-ethoxycarbonyl-piperidin-4-yl, 1-carbamoylmethyl-piperidin-4-yl, 1-(2-methoxycarbonyl)ethyl-piperidin-4-yl, 1-carbamoylmethyl-piperidin-4-ylmethyl, 1-(2-methoxycarbonyl)ethyl-piperidin-4-ylmethyl, 1-methanesulfonyl-piperidin-4-yl, 1-(2,2,2-trifluoroethyl)piperidin-4-yl, 1-(2,2,2-trifluoroethyl)piperidin-4-ylmethyl, 1-(2-cyanoethyl)-piperidin-4-yl, 1-(2-cyanoethyl)-piperidin-4-ylmethyl, tetrahydropyran-4-yl, 4-fluorophenyl, 3-chlorophenyl, 3-acetylphenyl, 3-cyanophenyl, 3-methoxycarbonyl-phenyl, 3-carbamoylphenyl, 3-(t-butyl-dimethylsilyloxy)phenyl, 3-hydroxyphenyl, 3-methanesulfonyloxyphenyl, 3-(N-methylcarbamoyl)phenyl, 3-(N,N-dimethylcarbamoyloxy)phenyl, 3-methylthiophenyl, 3-methanesulfinylphenyl, 2-(pyrrolidin-1-yl)ethyl, 2-(N,N-diethylamino)ethyl, 2-(N,N-dimethylamino)ethyl, piperid-4-yl, 1,3-diethoxyprop-2-yl, 2,2,2-trifluoroethyl, ethoxycarbonylmethyl, carboxymethyl, N,N-dimethylcarbamoylmethyl, 2-methylthioethyl, 3-(N,N-dimethylamino)-2,2-dimethylpropyl, 1-methylpiperid-4-yl, cyanomethyl, methoxycarbonylmethyl, 2-(triisopropylsilyloxy)ethyl, 2-hydroxyethyl, 2-trimethylsilylethyloxymethyl, 2-(piperidin-1-yl)ethyl, 3-(piperidin-1-yl)propyl, 2-(morpholin-4-yl)ethyl, 3-(morpholin-4-yl)propyl, 2-(2-oxo-imidazolidin-1-yl)ethyl, 2-(2-oxo-pyrrolidin-1-yl)ethyl, and 1,1-dioxo-tetrahydrothiophen-3-yl.

The compounds of the present invention can exist in unsolvated forms as well as solvated forms, including hydrated forms and are intended to be encompassed within the scope of the invention. Furthermore, as stated above, the present invention also includes all pharmaceutically acceptable salts of the compounds along with prodrug forms of the compounds and all stereoisomers whether in a pure chiral form or a racemic mixture of other forms of mixture.

Some compounds of the present invention can exist in a tautomeric form which are also intended to be encompassed within the scope of the present invention.

The compounds of formula I are capable of further forming pharmaceutically acceptable acid addition salts. All of these forms are also contemplated within the scope of the claimed invention.

Pharmaceutically acceptable acid addition salts of the compounds of formula I inlcude salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, pthalate, benzenesulfonate, toluenesulfonate, phenylacetate, citrate, lactate, maleate, tartarate, methanesulfonate, and the like. Also contemplated are salts of amino acids such as arginate, aspartate, glutamate and the like and gluconate, galacturonate (see, for example, Berge et al., "Pharmaceutical Salts," *J. of Pharmaceutical Science*, 1977, 66, 1–19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms somewhat in certain physical properties such as solubility in polar solvents, but otherwise the salts are equivalent to their respective free base for the purposes of the present invention.

Pharmaceutically acceptable base addition salts can be formed with metal ions or amines, such as alkali and alkaline earth metal ions or organic amines. Examples of metal ions which are used as cations include sodium, potassium, magnesium, calcium, and the like. Examples of suitable amines are N,N'-dibenzylethylenediamine, chlororocaine, choline, diethanolamine, ethylenediamine, N-methylglucamine, and procaine (see, for example, Berge et al., supra).

The base addition salts of acidic compounds can be prepared by contacting the free acid form with a sufficient amount of the desired base to produce the salt in the conventional manner. The free acid form can be regenerated by contacting the salt form with an acid and isolating the free acid in the conventional manner. The free acid forms may differ from their respective salt forms somewhat in certain physical properties such as solubility in polar solvents, but otherwise the salts are equivalent to their respective free acid for the purposes of the present invention.

Another aspect of the present invention provides a compound of the formula:

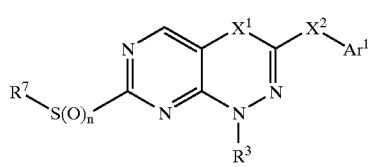

II wherein $R^3$, $X^1$, $X^2$, and $Ar^1$ are those defined above; n is 0, 1, or 2, preferably 0 or 1preferably 1; and $R^7$ is alkyl.

Compounds of Formula II are useful in preparing compounds of Formula I as discussed in detail below.

Processes for Preparing the Compounds

The compounds of the present invention can be prepared by a variety of methods, using procedures well-known to those of skill in the art. The following schemes illustrate the processes of making the compounds of the invention.

Treatment of a compound of formula 1 (obtained according to the literature procedure: for X=Br, see Barrett, H. W.; Goodman, I.; Ditter, K., *J. Am. Chem. Soc.,* 1948, 70, 1753; for X=I see Sakamoto, T.; Kondo, Y.; Watanabe, R.; Yamanaka, H., *Chem. Pharm. Bull.,* 1986, 34, 2719) with alkyl hydrazines provides a compound of formula 2, which is then acylated to give a compound of formula 3. The cyclization of 3 in the presence of sodium hydroxide and triethylamine gives 4 (see Elliott, A. J.; Gibson, M. S., *J. Org. Chem.* 1980, 45, 3677). The reaction is typically carried out with DMF or NMP at 120° C.

Oxidation of compound 4 with an oxidizing agent, such as 3-chloroperbenzoic acid (i.e., MCPBA) and Oxone®, provides a sulfone 5 which can be converted into a variety of target compounds. Typically the oxidation of 5 is carried out in a solvent which is inert under the conditions of the oxidation. For example, when MCPBA is used as the oxidizing agent, the solvent is preferably a halogenated aliphatic hydrocarbon, especially dichloromethane. When Oxone® is used as the oxidizing agent, the typical solvent is water and/or tetrahydrofuran. The reaction temperature depends on the solvent used. For an organic solvent, the reaction temperature is generally at about −20° C. to about 50° C., preferably about 0° C. to about room temperature. When water is used as the solvent, the reaction temperature is generally from about 0° C. to about 50° C., preferably about 0° C. to about room temperature.

Reaction of compound 5 with an amine of formula $R^1R^2NH$, wherein $R^1$ and $R^2$ are as defined herein above, affords a compound of Formula I. The reaction can be carried out in the presence or absence of a solvent. Conveniently, the reaction is carried out at temperatures of from about 0° C. to about 200° C., more preferably about room temperature to about 150° C.

Alternatively compounds with a formula I when R3 is aryl can be prepared according to Scheme 2.

Scheme 1

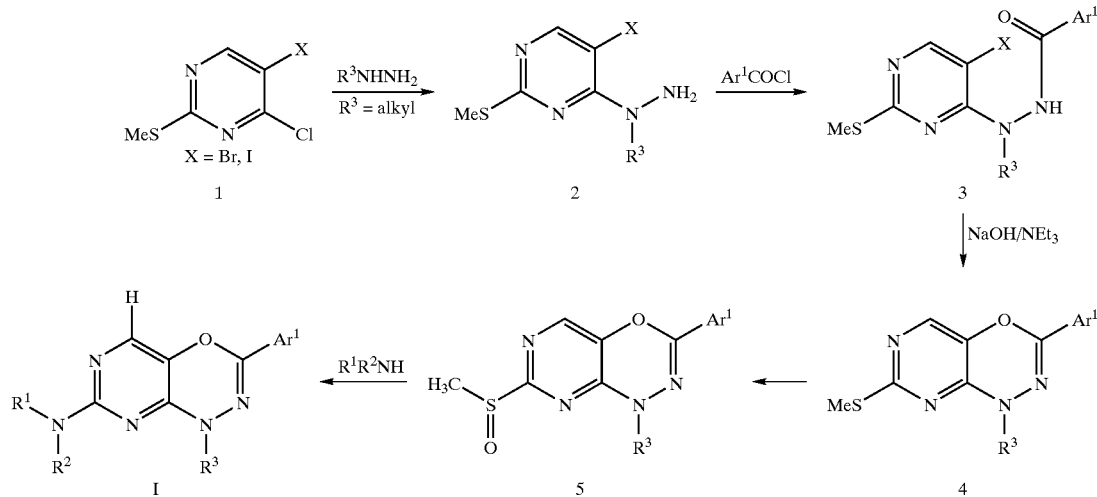

Scheme 2

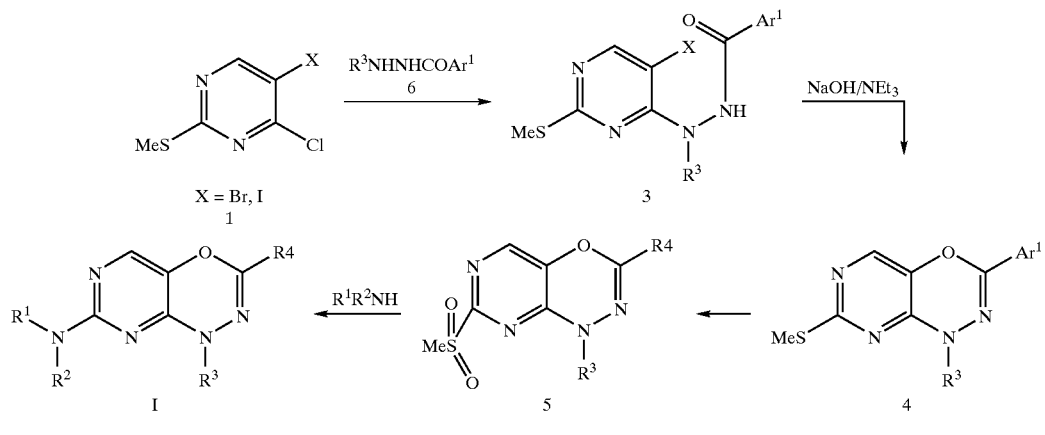

Reaction of 1 with 6 yields a compound of a formula 3. The rest of the steps are similar to those outline in Scheme 1.

One of skill in the art will understand that certain modifications to the above schemes are contemplated and within the scope of the present invention. For example, certain steps will involve the use of protecting groups for functional groups that are not compatible with particular reaction conditions.

Pharmaceutical Compositions Containing the Compounds

The compounds of formula I and the pharmaceutically acceptable salts of basic compounds of formula I with acids can be used as medicaments, e.g. in the form of pharmaceutical preparations. The pharmaceutical preparations can be administered enterally, e.g. orally in the form of tablets, coated tablets, dragees, hard and soft gelatine capsules, solutions, emulsions or suspensions, nasally, e.g. in the form of nasal sprays, or rectally, e.g. in the form of suppositories. However, they may also be administered parenterally, e.g. in the form of injection solutions.

The compounds of formula I and their aforementioned pharmaceutically acceptable salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain therapeutically valuable substances other than the compounds of formula I and their aforementioned pharmaceutically acceptable salts.

Medicaments which contain a compound of formula I or a pharmaceutically acceptable salt of a basic compound of formula I with an acid in association with a compatible pharmaceutical carrier material are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of formula I and their aforementioned pharmaceutically acceptable salts can be used in accordance with the invention as therapeutically active substances, especially as anti-inflammatory agents or for the prevention of graft rejection following transplant surgery. The dosage can vary within wide limits and will, of course, be fitted to the individual requirements in each particular case. In general, in the case of administration to adults a convenient daily dosage should be about 0.1 mg/kg to about 100 mg/kg, preferably about 0.5 mg/kg to about 5 mg/kg. The daily dosage may be administered as a single dose or in divided doses and, in addition, the upper dosage limit referred to earlier may be exceeded when this is found to be indicated.

Finally, the use of compounds of formula I and their aforementioned pharmaceutically acceptable salts for the production of medicaments, especially in the treatment or prophylaxis of inflammatory, immunological, oncological, bronchopulmonary, dermatological and cardiovascular disorders, in the treatment of asthma, central nervous system disorders or diabetic complications or for the prevention of graft rejection following transplant surgery, is also an object of the invention.

Methods of Using the Compounds and Compositions

Compounds of Formula I would be useful for, but not limited to, the treatment of any disorder or disease state in a human, or other mammal, which is exacerbated or caused by excessive or unregulated TNF or p38 kinase production by such mammal. Accordingly, the present invention provides a method of treating a cytokine-mediated disease which comprises administering an effective cytokine-interfering amount of a compound of Formula I, or a pharmaceutically acceptable salt or tautomer thereof.

Compounds of Formula I would be useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of influenza, multiple sclerosis, cancer, diabetes, systemic lupus erthrematosis (SLE), skin-related conditions such as psoriasis, eczema, burns, dermatitis, keloid formation, and scar tissue formation. Compounds of the invention also would be useful to treat gastrointestinal conditions such as inflammatory bowel disease, Crohn's disease, gastritis, irritable bowel disease and ulcerative colitis. The compounds would also be useful in the treatment of ophthalmic diseases, such as retinitis, retinopathies, uveitis, ocular photophobia, and of acute injury to the eye tissue. Compounds of the invention also would be useful for treatment of angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds of the invention may also be useful for preventing the production of cyclooxygenase-2.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, LTB$_4$ antagonists and LTA$_4$ hydrolase inhibitors.

As used herein, the term "TNF mediated disorder" refers to any and all disorders and disease states in which TNF plays a role, either by control of TNF itself, or by TNF causing another monokine to be released, such as but not limited to, IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

The compounds of Formula I are also cellular antiproliferative agents and useful in treating proliferative disorders such as cancer. Specific tumors include small cell lung carcinoma, human breast cancer; low grade human bladder carcinomas and human colorectal cancer Testing The ability of the compounds of the present invention to inhibit p38 MAP kinase was demonstrated by the in vitro assay described in Example 57. The ability of the compounds of the present invention to inhibit the release of TNF-α was demonstrated by the in vitro and the in vivo assays described in detail in Examples 58 and 59, respectively. The anti-inflammatory activity of the compounds of this invention can be determined utilizing adjuvant induced arthritis in rats assay described in Example 60.

The ability of the compounds of the present invention to inhibit FGRR kinase may be determined by procedures such as those described in WO99/61444 and WO98/34867.

Additional objects, advantages, and novel features of this invention will become apparent to those skilled in the art upon examination of the following illustrative examples thereof, which are not intended to be limiting.

EXAMPLES

Example 1

This example illustrates synthesis of 2-methyl-4-(2-chlorophenyl)-6-(tetrahydropyranyl-4-amino)-4H-1,3,4-pyrimido[4,5-e]oxadiazine using the method described under Scheme 1.

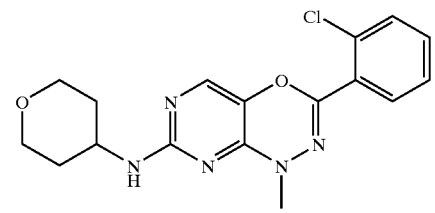

Step 1. Preparation of 5-iodo-4-(1-methylhydrazino)-2-methylthiopyrimidine.

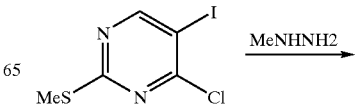

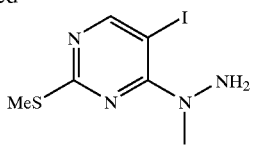

To a solution of 6.27 g (22 mmol) of 5-iodo-4-chloro-2-methylthiopyrimidine in 100 mL of dichloromethane at 0° C. was added slowly methyl hydrazine (Aldrich, 12 mL). The mixture was stirred from 0° C. to room temperature for 2 h and then concentrated. EtOAc was added and washed with brine, dried, and evaporated to give the product. MS: 297 (M+H).

Step 2. Preparation of 5-bromo-4-(1-methyl-2-(2-chlorobenzoyl)hydrazino)-2-methylthiopyrimidine.

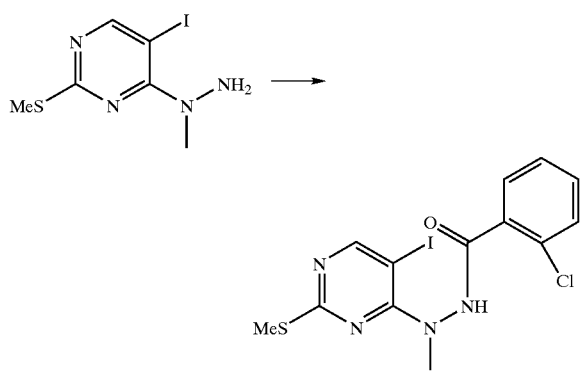

To the product obtained in step 1 (1.68 g, 5.7 mmol) in ether (100 mL) and THF (10 mL) added triethyl amine (2 mL) and 2'-chlorobenzoyl chloride (1.2 mL) at 0° C. and the mixture was stirred at room temperature for 6 h. EtOAc (100 mL) and brine (50 mL) were added. The white solids were filtered, washed with water and EtOAc, and dried to give the desired product (0.58 g). The filtrate was separated, washed with brine, dried, and evaporated to give the crude product. Trituration with ether to give additional 0.67 g of the product.

Step 3. Preparation of 2-methyl-4-(2-chlorophenyl)-6-(methylthio)-4H-1,3,4-pyrimido[4,5-e]oxadiazine.

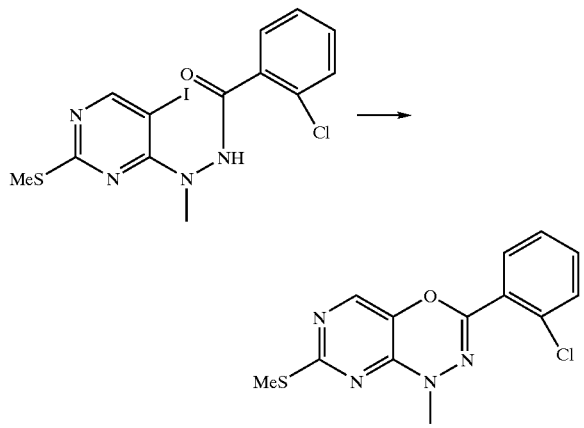

To the product obtained in step 2 (1.01 g, 2.32 mmol) in dry DMF (26 mL) was added triethyl amine (3 mL) and sodium hydroxide (powder, 0.16 g). The mixture was heated at 110° C. for 8 h and cooled to room temperature. EtOAc (100 mL) was added, washed with brine (3×50 mL), dried and evaporated to give yellow solids. Trituration with ether gave the desired product (0.34 g). MP: 142.5–144.3° C. MS: 307.1 (M+H).

Step 4. Preparation of 2-methyl-4-(2-chlorophenyl)-6-(methylsulfinyl)-4H-1,3,4-pyrimido[4,5-e]oxadiazine.

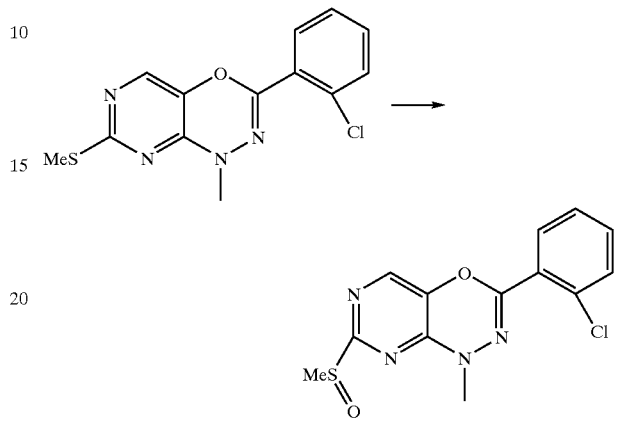

To the sulfide (0.367 g, 1.2 mmol) obtained in Step 3 in THF (12 mL) was added a solution of Oxone (Aldrich, 0.89 g) in water (12 mL) at 0° C. The mixture was then stirred at room temperature for 4 hours. Ethyl acetate (50 mL) and water (50 mL) were added. The organic phase was separated, washed with water (2×20 mL), dried, and evaporated to give the sulfoxide (0.40 g).

Step 5. Preparation of 2-methyl-4-(2-chlorophenyl)-6-(tetrahydropyranyl-4-amino)-4H-1,3,4-pyrimido[4,5-e]oxadiazine.

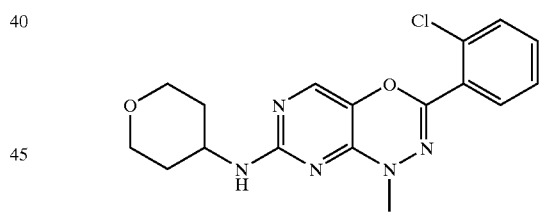

A mixture of the sulfoxide obtained above (400 mg) and 4-aminotetrahydropyran (350 mg) in NMP (0.3 mL) was heated at 110° C. for 24 hours. Ethyl acetate (60 mL) and water (25 mL) were added. The organic layer was separated, washed with brine, dried, and evaporated. The crude product was purified by preparative TLC (silica gel, 50% EtOAc/hexanes) to give 180 mg of the final product. MP: 171.0–172.1° C. MS: 360.2 (M+H).

Example 2

This example illustrates a method for producing 2-methyl-4-(2,6-dichlorophenyl)-6-(3-methylsulfinylphenyl-amino)-4H-1,3,4-pyrimido[4,5-e]oxadiazine.

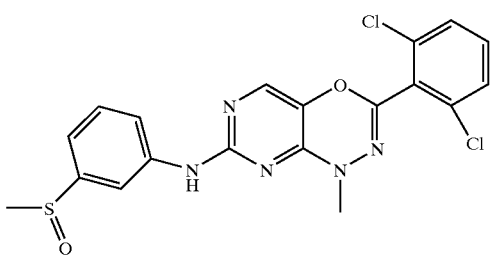

Step 1. Preparation of 5-bromo-4-(1-methyl-2-(2,6-dichlorobenzoyl)hydrazino)-2-methylthiopyrimidine.

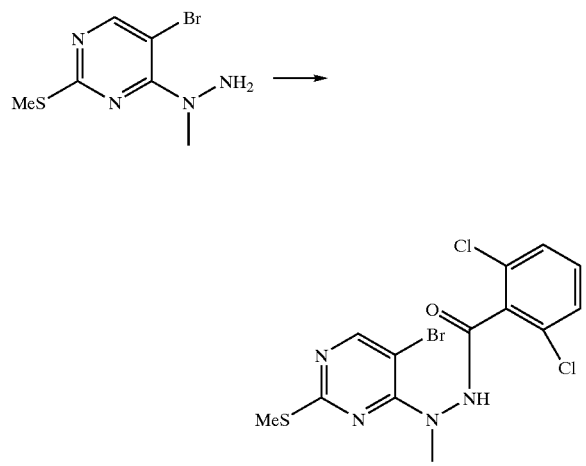

To 5-bromo-4-(1-methyl hydrazino)-2-methylthiopyrimidine prepared similar to step 1 in Example 1 (1.55 g, 6.2 mmol) in dichloromethane (30 mL) and triethyl amine (1.8 mL) at 0° C. was added 2,6-dichlorobenzoyl chloride (1.0 mL). The mixture was stirred at 0° C. to room temperature overnight. The solids formed were filtered, washed with water and ether, and dried to give 2.61 g of the product. MP: 254.4–256.5° C.

Step 2. Preparation of 2-methyl-4-(2,6-dichlorophenyl)-6-(methylthio)-4H-1,3,4-pyrimido[4,5-e]oxadiazine.

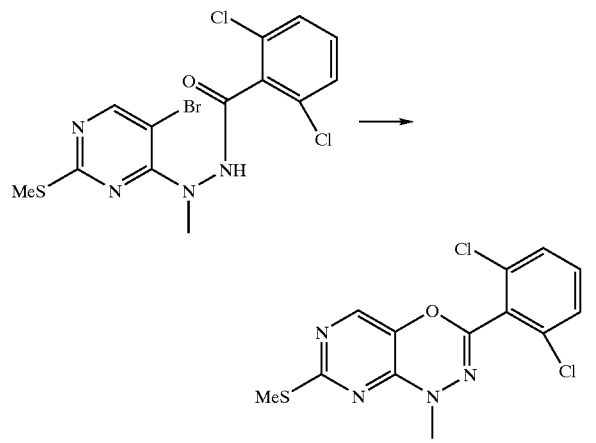

To the product in the step 1(1.97 g, 4.67 mmol) in dry DMF (25 mL) were added triethylamine (6.5 mL) and sodium hydroxide (0.77 g). The mixture was heated at 110° C. for two days. The mixture was cooled to room temperature, diluted with EtOAc (100 mL), and washed with brine (3×50 mL), dried, and evaporated to give the crude product. Column chromatography purification (20% EtOAc/hexanes) gave 0.61 g of the pure product.

Step 3. Preparation of 2-methyl-4-(2-chlorophenyl)-6-(methylsulfinyl)-4H-1,3,4-pyrimido[4,5-e]oxadiazine.

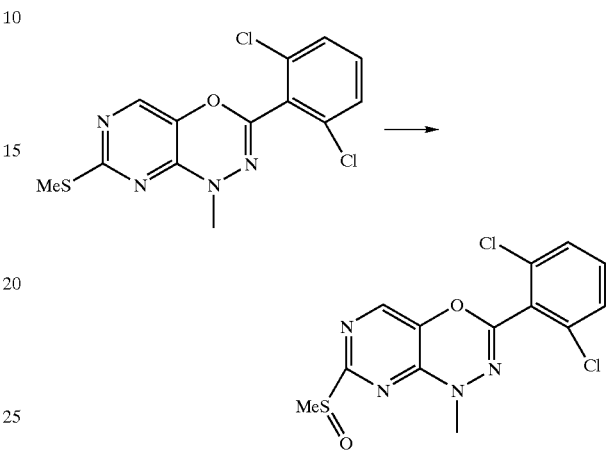

To the sulfide (0.137 g, 0.4 mmol) obtained in Step 2 in THF (4 mL) was added a solution of Oxone (Aldrich, 0.323 g) in water (3 mL) at 0° C. The mixture was then stirred at room temperature for 3 hours. Ethyl acetate (50 mL) and water (50 mL) were added. The organic phase was separated, washed with water (2×20 mL), dried, and evaporated to give the sulfoxide (0.123 g).

Step 4. Preparation of 2-methyl-4-(2,6-dichlorophenyl)-6-(3-methylthiophenyl-amino)-4H-1,3,4-pyrimido[4,5-e]oxadiazine.

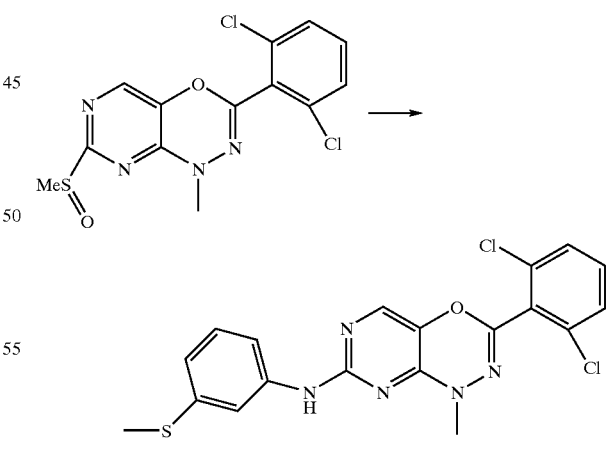

The sulfoxide (22 mg) and 3-methylthioaniline (84 mg) were heated at 130° C. for 6 h. The mixture was cooled to room temperature, diluted with EtOAc (30 mL), washed with brine, dried, and evaporated. The crude product was purified by preparative TLC (30% EtOAc/hexanes) to give 14 mg of the solids. MS: 432, 434, 436 (M+H).

35

Step 5. Preparatino of 2-methyl-4-(2,6-dichlorophenyl)-6-(3-methylsulfinylphenyl-amino)-4H-1,3,4-pyrimido[4,5-e]oxadiazine.

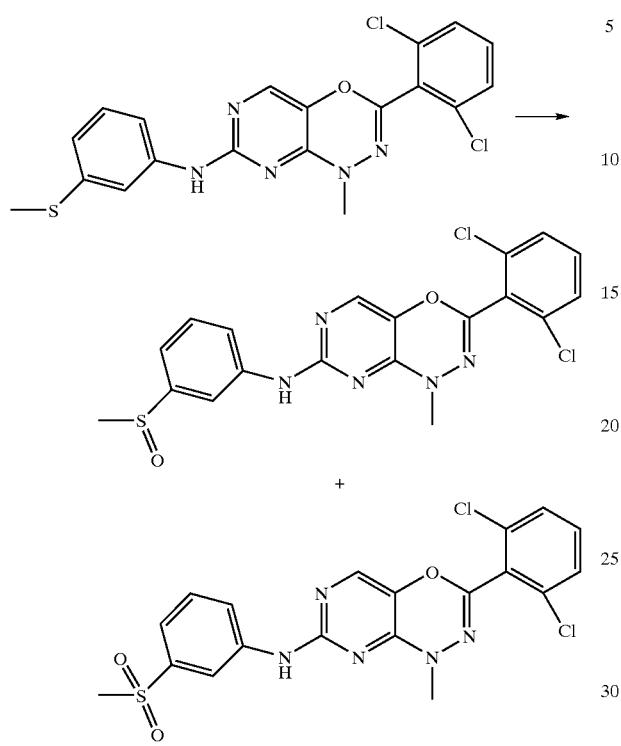

The sulfide obtained in step 4 (40 mg) was dissolved in THF (1 mL) and stirred with a solution of Oxone (55 mg) in water (1 mL) at 0° C. to room temperature for 30 minutes. EtOAc was added, washed with brine, dried, and evaporated. The crude products were purified by preparative TLC (50% EtOAc/hexanes) to give 2-methyl-4-(2,6-dichlorophenyl)-6-(3-methylsulfinylphenyl-amino)-4H-1,3,4-pyrimido [4,5-e]oxadiazine (MS: 448 (M+H)) and 2-methyl-4-(2,6-dichlorophenyl)-6-(3-methylsulfonylphenyl-amino)-4H-1,3,4-pyrimido [4,5-e]oxadiazine (MS: 464, 466 (M+H)).

Example 3

This example illustrates a method for producing 4-methoxy-benzoic acid N'-(5-bromo-2-methylsulfanyl-pyrimidin-4-yl)-N'-methyl-hydrazide.

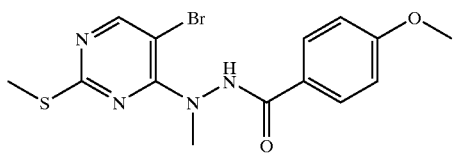

To a solution of N-(5-bromo-2-methylsulfanyl-pyrimidin-4-yl)-N-methyl-hydrazine (1.0 g, 4.0 mmol) and triethylamine (1.2 mL, 8.4 mmol) in $CH_2Cl_2$ (20 mL) was added p-anisoyl chloride (1.54 g, 9.04 mmol) (Aldrich) in $CH_2Cl_2$ (5 mL) at 0° C. The reaction mixture was stirred at room temperature for 1 day. It was diluted with ethyl acetate and water. The organic layer was washed with water and brine, dried with $MgSO_4$, filtered and concentrated. The residue was purified by flash chromatography (Biotage) eluting with EtOAc/$CH_2Cl_2$ (5:95) to afford the product. (Yield 0.90 g, 59%).

36

Example 4

This example illustrates a method for producing 3-(4-methoxy-phenyl)-1-methyl-7-methylsulfanyl-1H-pyrimido[4,5-e][1,3,4]oxadiazine.

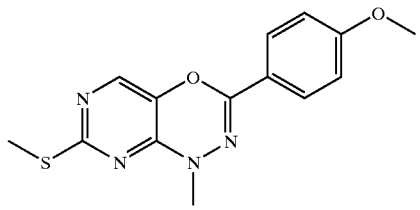

A mixture of 4-methoxy-benzoic acid N'-(5-bromo-2-methylsulfanyl-pyrimidin-4-yl)-N'-methyl-hydrazide (0.9 g, 2.35 mmol), triethylamine (2.5 mL) and NaOH (0.12 g, 2.94 mmol) was heated at 130° C. for 2 days. It was diluted with ethyl acetate and water. The organic layer was washed with water and brine, dried with $MgSO_4$, filtered and concentrated. The residue was purified by flash chromatography (Biotage) eluting with EtOAc/hexanes (2:3) to afford the product. (Yield 0.23 g, 32%).

Example 5

This example illustrates a method for producing 7-methanesulfinyl-3-(4-methoxyphenyl)-1-methyl-1H-pyrimido[4,5-e][1,3,4]oxadiazine.

To a solution of 3-(4-methoxy-phenyl)-1-methyl-7-methylsulfanyl-1H-pyrimido[4,5-e][1,3,4]oxadiazine (0.23 g, 0.76 mmol) in THF at 0° C. was added Oxone® (0.62 g, 1.01 mm (Aldrich) in water (5 mL). The reaction mixture was stirred at 0° C. for 3 h. It was diluted with ethyl acetate and water. The organic layer was washed with water and brine, dried with $MgSO_4$, filtered and concentrated. The residue was washed with hot EtOAc and dried to give the product. (Yield 0.20 g, 83%).

Example 6

This example illustrates a method for producing [3-(4-methoxy-phenyl)-1-methyl-1H-pyrimido[4,5-e][1,3,4]oxadiazin-7-yl]-phenyl-amine.

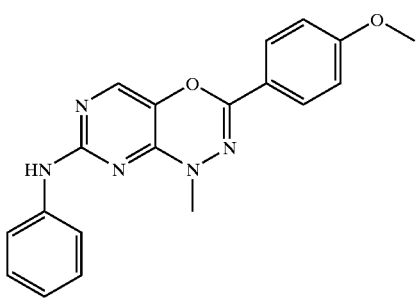

A mixture of 7-methanesulfinyl-3-(4-methoxy-phenyl)-1-methyl-1H-pyrimido[4,5-e][1,3,4]oxadiazine (0.20 g, 0.63 mmol) and aniline (4 mL) (Aldrich) was placed in a microwave reactor (SmithSynthesizer™). The reaction mixture was heated at 160° C. for 1 h. The precipitate formed was collected by filtration and purified by flash chromatography eluting with EtOAc/hexanes (2:3) to afford the product. (Yield 65 mg, 30%).

HRMS m/z Calculated for $C_{19}H_{17}N_5O_2$ [(M+H)$^+$]: 348.1455. Found: 348.1458.

Example 7

This example illustrates a method for producing 4-methoxy-2-methyl-benzoic acid N'-(5-bromo-2-methylsulfanyl-pyrimidin-4-yl)-N'-methyl-hydrazide

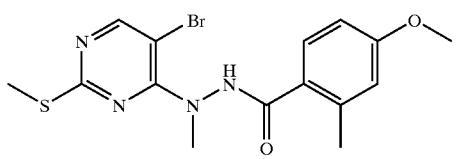

To a solution of N-(5-bromo-2-methylsulfanyl-pyrimidin-4-yl)-N-methyl-hydrazine (0.24 g, 0.97 mmol) and triethylamine (0.68 mL, 4.85 mmol) in $CH_2Cl_2$ (15 mL) was added 4-methoxy-2-methyl-benzoyl chloride (0.36 g, 1.95 mmol) (from 4-methoxy-2-methyl-benzoic acid (Aldrich) and $SOCl_2$) in $CH_2Cl_2$ (5 mL). The reaction mixture was stirred at room temperature for 18 h. The precipitate formed was collected by filtration and dried to give product. The mother liquid was dilute with EtOAc and washed with water and brine, dried with $MgSO_4$, filtered and concentrated. This residue was washed with hot $CH_2Cl_2$ and dried to give a second crop of product. (Combined yield 0.35 g, 90%).

Example 8

This example illustrates a method for producing 3-(4-Methoxy-2-methyl-phenyl)-1-methyl-7-methylsulfanyl-1H-pyrimido[4,5-e][1,3,4]oxadiazine.

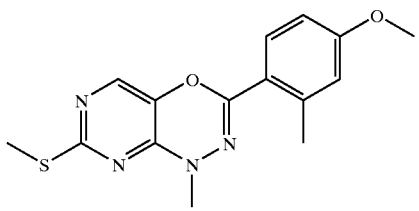

A mixture of 4-methoxy-2-methyl-benzoic acid N'-(5-bromo-2-methylsulfanyl-pyrimidin-4-yl)-N'-methyl-hydrazide (0.35 g, 0.88 mmol), triethylamine (1.5 mL) and NaOH powder (50 mg, 1.25 mmol) in DMF (4 mL) were placed in a microwave reactor (SmithSynthesizer™). The reaction mixture was heated at 200° C. for 1 h. It was diluted with ethyl acetate and water. The organic layer was washed with brine, dried with $MgSO_4$, filtered and concentrated. The residue was dried to give the product. (Yield 0.24 g, 83%).

Example 9

This example illustrates a method for producing 7-methanesulfinyl-3-(4-methoxy-2-methyl-phenyl)-1-methyl-1H-pyrimido[4,5-e][1,3,4]oxadiazine.

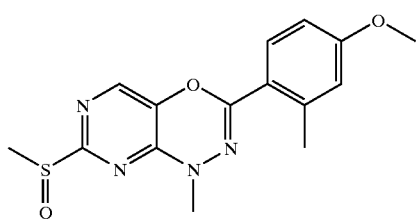

To a solution of 3-(4-methoxy-2-methylphenyl)-1-methyl-7-methylsulfanyl-1H-pyrimido[4,5-e][1,3,4]oxadiazine (0.24 g, 0.76 mmol) in THF (10 mL) at 0° C. was added Oxone® (0.62 g, 1.01 mmol) (Aldrich) in water (5 mL). The reaction mixture was stirred at 0° C. for 3 h. It was diluted with $CH_2Cl_2$. The organic layer was washed with water and brine, dried with $MgSO_4$, filtered and concentrated. The residue was recrystallized from EtOAc and dried to give the product. (Yield 0.21 g, 84%)

Example 10

This example illustrates a method for producing [3-(4-methoxy-2-methyl-phenyl)-1-methyl-1H-pyrimido[4,5-e][1,3,4]oxadiazin-7-yl]-phenylamine.

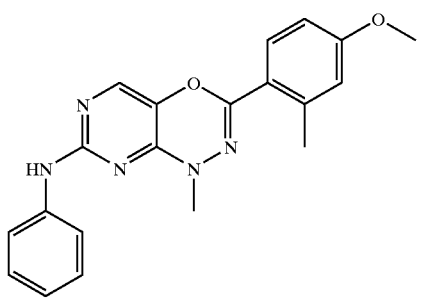

A mixture of 7-methanesulfinyl-3-(4-methoxy-2-methyl-phenyl)-1-methyl-1H-pyrimido[4,5-e][1,3,4]oxadiazine (0.21 g, 0.63 mmol) and aniline (2 mL) (Aldrich) was placed in a microwave reactor (SmithSynthesizer™). The reaction mixture was heated at 200° C. for 1 h. The reaction mixture was diluted with MeOH. The precipitate was collected by filtration, washed with isopropanol and dried to give the product. (Yield 85 mg, 37%).

HRMS m/z Calculated for $C_{20}H_{19}N_5O_2$ [(M+H)$^+$]: 362.1612. Found: 362.1614.

Example 11

This example illustrates a method for producing 2,6-dichloro-benzoic acid N'-(5-bromo-2-methylsulfanyl-pyrimidin-4-yl)-N'-methyl-hydrazide.

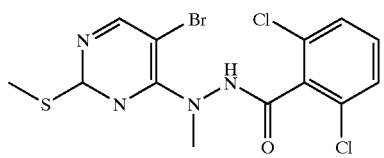

To a solution of N-(5-bromo-2-methylsulfanyl-pyrimidin-4-yl)-N-methyl-hydrazine (0.40 g, 1.61 mmol) and triethylamine (1.12 mL, 8.05 mmol) in $CH_2Cl_2$ (15 mL) was added 2,6-dichlorobenzoyl chloride (0.46 mL, 3.21 mmol) (Aldrich). The reaction mixture was stirred at room temperature for 18 h. The precipitate was collected by filtration, washed with $CH_2Cl_2$ and dried to give the product. (Yield 0.52 g, 76%).

Example 12

This example illustrates a method for producing 3-(2,6-dichlorophenyl)-1-methyl-7-methylsulfanyl-1H-pyrimido[4,5-e][1,3,4]oxadiazine.

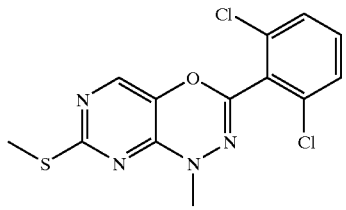

A mixture of 2,6-dichloro-benzoic acid N'-(5-bromo-2-methylsulfanyl-pyrimidin-4-yl)-N'-methyl-hydrazide (0.52 g, 1.23 mmol), triethylamine (3.0 mL) and NaOH powder (100 mg, 2.5 mmol) in DMF (4 mL) was placed in a microwave reactor (SmithSynthesizer™). The reaction mixture was heated at 200° C. for 1 h. It was diluted with ethyl acetate and water. The organic layer was washed with brine, dried with $MgSO_4$, filtered and concentrated. The residue was purified by flash chromatography eluting with EtOAc/$CH_2Cl_2$ (5:95) to afford the product. (Yield 0.31 g, 74%).

Example 13

This example illustrates a method for producing 7-methanesulfinyl-3-(2,6-dichlorophenyl)-1-methyl-1H-pyrimido[4,5-e][1,3,4]oxadiazine.

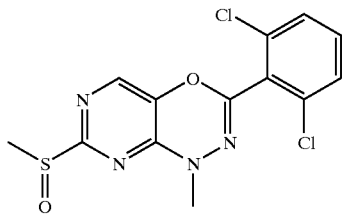

To a solution of 3-(2,6-dichlorophenyl)-1-methyl-7-methylsulfanyl-1H-pyrimido[4,5-e][1,3,4]oxadiazine (0.31 g, 0.91 mmol) in THF (10 mL) at 0° C. was added Oxone® (0.74 g, 1.33 mmol) (Aldrich) in water (6 mL). The reaction mixture was stirred at 0° C. for 4 h. It was diluted with $CH_2Cl_2$. The organic layer was washed with water and brine, dried with $MgSO_4$, filtered and concentrated. The residue was dried to give the product. (Yield 0.29 g, 88%).

Example 14

This example illustrates a method for producing [3-(2,6-dichlorophenyl)-1-methyl-1H-pyrimido[4,5-e][1,3,4]oxadiazin-7-yl]-phenyl-amine.

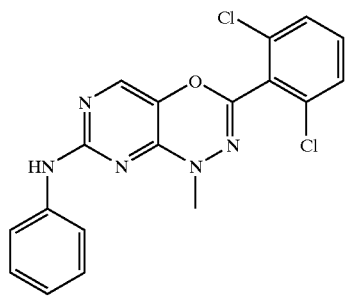

A mixture of 7-methanesulfinyl-3-(2,6-dichloro-phenyl)-1-methyl-1H-pyrimido[4,5-e][1,3,4]oxadiazine (0.14 g, 0.39 mmol) and aniline (2 mL) (Aldrich) was placed in a microwave reactor (SmithSynthesizer™). The reaction mixture was heated at 200° C. for 1 h. The reaction mixture was diluted with MeOH. The precipitate was collected by filtration, washed with isopropanol and dried to give the product. (Yield 30 mg, 20%).

HRMS m/z Calculated for $C_{18}H_{13}Cl_2N_5O$ $[(M+H)^+]$: 386.0570. Found: 386.0574.

Example 15

This example illustrates a method for producing [3-(2,6-Dichloro-phenyl)-1-methyl-1H-pyrimido[4,5-e][1,3,4]oxadiazin-7-yl]-(4-fluoro-phenyl)-amine.

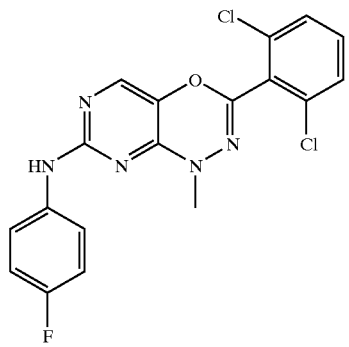

A mixture of 7-methanesulfinyl-3-(2,6-dichloro-phenyl)-1-methyl-1H-pyrimido[4,5-e][1,3,4]oxadiazine (0.14 g, 0.39 mmol) and 4-fluoroaniline (2 mL) (Acros) was placed in a microwave reactor (SmithSynthesizer™). The reaction mixture was heated at 200° C. for 1 h. The reaction mixture was concentrated. The residue was washed with isopropanol and dried to give the product. (Yield 52 mg, 33%).

HRMS m/z Calculated for $C_{18}H_{12}Cl_2FN_5O$ $[(M+H)^+]$: 404.0476. Found: 404.0482.

Example 16

This example illustrates a method for producing [3-(2,6-Dichloro-phenyl)-1-methyl-1H-pyrimido[4,5-e][1,3,4]oxadiazin-7-yl]-(3-chloro-phenyl)-amine.

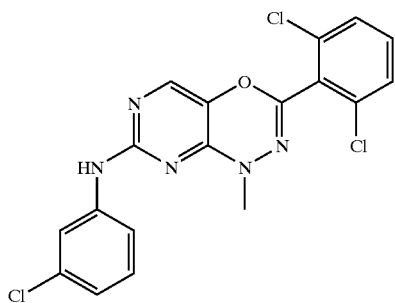

A mixture of 7-methanesulfinyl-3-(2,6-dichloro-phenyl)-1-methyl-1H-pyrimido[4,5-e][1,3,4]oxadiazine (0.14 g, 0.39 mmol) and 3-chloroaniline (2 mL) (Aldrich) were placed in a microwave reactor (SmithSynthesizer™). The reaction mixture was heated at 200° C. for 1 h. The reaction mixture was concentrated. The residue was washed with methanol and dried to give the product. (Yield 0.1 g, 77%).

HRMS m/z Calculated for $C_{18}H_{12}Cl_3N_5O$ [(M+H)$^+$]: 420.0180. Found: 420.0183.

Example 17

This example illustrates a method for producing 1-{3-[3-(2,6-dichloro-phenyl)-1-methyl-1H-pyrimido[4,5-e][1,3,4]oxadiazin-7-ylamino]-phenyl}-ethanone.

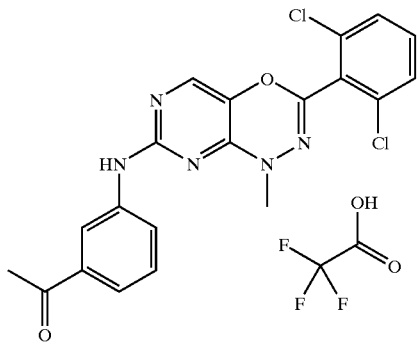

A solution of 7-methanesulfinyl-3-(2,6-dichloro-phenyl)-1-methyl-1H-pyrimido[4,5-e][1,3,4]oxadiazine (0.10 g, 0.28 mmol), 1-(3-amino-phenyl)-ethanone (75.6 mg, 0.56 mmol) (Aldrich) and p-toluenesulfonic acid monohydrate (53.2 mg, 0.28 mmol) (Aldrich) in isopropanol (4 mL) was placed in a microwave reactor (SmithSynthesizer™). The reaction mixture was heated at 160° C. for 1 h. The reaction mixture was concentrated and purified by RP-HPLC (C-18, eluting with MeCN/H$_2$O containing 0.1% TFA) to afford the product. (Yield 94 mg, 62%).

HRMS m/z Calculated for $C_{20}H_{15}Cl_2N_5O_2$ [(M+H)$^+$]: 428.0676. Found: 428.0676.

Example 18

This example illustrates a method for producing 3-[3-(2,6-dichloro-phenyl)-1-methyl-1H-pyrimido[4,5-e][1,3,4]oxadiazin-7-ylamino]-benzonitrile.

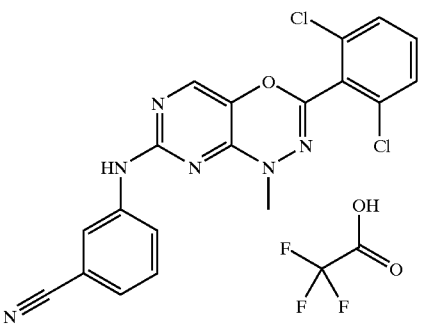

A solution of 7-methanesulfinyl-3-(2,6-dichloro-phenyl)-1-methyl-1H-pyrimido[4,5-e][1,3,4]oxadiazine (0.10 g, 0.28 mmol), m-aminobenzonitrile (66 mg, 0.56 mmol) (Pfaltz-Bauer) and p-toluenesulfonic acid monohydrate (53.3 mg, 0.28 mmol) (Aldrich) in isopropanol (4 mL) was placed in a microwave reactor (SmithSynthesizer™). The reaction mixture was heated at 160° C. for 1 h. The reaction mixture was concentrated and purified by RP-HPLC (C-18, eluting with MeCN/H$_2$O containing 0.1% TFA) to afford the product. (Yield 36 mg, 24%).

HRMS m/z Calculated for $C_{19}H_{12}Cl_2N_6O$ [(M+H)$^+$]: 411.0523. Found: 411.0524.

Example 19

This example illustrates a method for producing 3-[3-(2,6-dichloro-phenyl)-1-methyl-1H-pyrimido[4,5-e][1,3,4]oxadiazin-7-ylamino]-benzoic acid methyl ester.

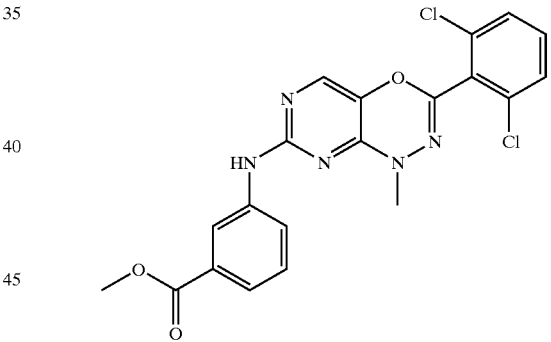

A solution of 7-methanesulfinyl-3-(2,6-dichloro-phenyl)-1-methyl-1H-pyrimido[4,5-e][1,3,4]oxadiazine (0.10 g, 0.28 mmol), methyl 3-aminobenzoate (84.6 mg, 0.56 mmol) (Lancaster) and p-toluenesulfonic acid monohydrate (53.3 mg, 0.28 mmol) (Aldrich) in isopropanol (4 mL) was placed in a microwave reactor (SmithSynthesizer™). The reaction mixture was heated at 160° C. for 1 h. The reaction mixture was concentrated. The precipitate was collected by filtration and washed with isopropanol and dried to give the product. (Yield 96 mg, 80%).

HRMS m/z Calculated for $C_{20}H_{15}Cl_2N_5O_3$ [(M+H)$^+$]: 444.0625. Found: 444.0628.

Example 20

This example illustrates a method for producing 3-[3-(2,6-dichloro-phenyl)-1-methyl-1H-pyrimido[4,5-e][1,3,4]oxadiazin-7-ylamino]-benzamide.

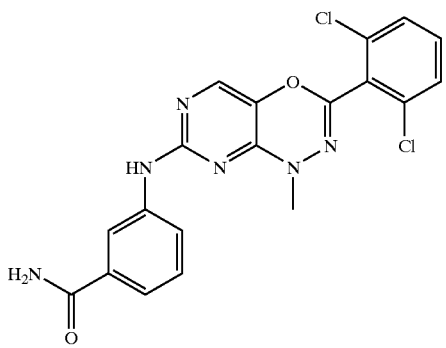

To a solution of 3-[3-(2,6-dichloro-phenyl)-1-methyl-1H-pyrimido[4,5-e][1,3,4]oxadiazin-7-ylamino]-benzonitrile (65 mg, 0.16 mmol) in acetone (5 mL) at 0° C. was added 1N NaOH solution (0.4 mL) and 30% hydrogen peroxide (0.2 mL). The reaction mixture was stirred at 0° C. for 5 h. The precipitate was collected by filtration, washed with water and dried to give the product. (Yield 60 mg, 87%).

HRMS m/z Calculated for $C_{19}H_{14}Cl_2N_6O_2$ [(M+H)$^+$]: 429.0628. Found: 429.0632.

Example 21

This example illustrates a method for producing 3-(tert-butyl-dimethyl-silanyloxy)-phenylamine.

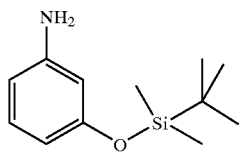

To a solution of m-aminophenol (11.0 g, 9.16 mmol) (Aldrich) in $CH_2Cl_2$ (50 mL) was added imidazole (3.12 g, 45.8 mmol) (Aldrich) and t-butyldimethylsilyl chloride (4.14 g, 27.49 mmol) (Aldrich). The reaction mixture was stirred at room temperature for 1 d. It was concentrated under reduced pressure. The residue was diluted with ethyl acetate (50 mL) and water (50 mL). The organic layer was washed with 1N NaOH solution, water and brine, dried with $MgSO_4$, filtered and concentrated. The residue was purified by flash chromatography eluting with EtOAc/$CH_2Cl_2$ (1:99) to afford the product. (Yield 1.85 g, 90%).

Example 22

This example illustrates a method for producing [3-(tert-butyl-dimethyl-silanyloxy)-phenyl]-[3-(2,6-dichloro-phenyl)-1-methyl-1H-pyrimido[4,5-e][1,3,4]oxadiazin-7-yl]-amine.

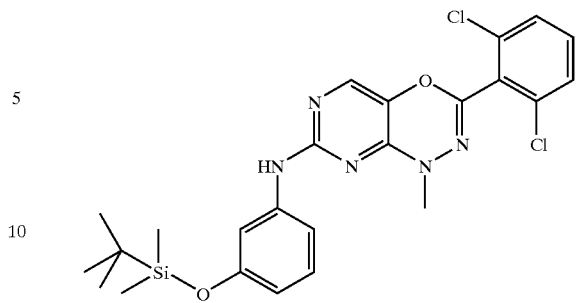

A solution of 7-methanesulfinyl-3-(2,6-dichloro-phenyl)-1-methyl-1H-pyrimido[4,5-e][1,3,4]oxadiazine (0.15 g, 0.42 mmol), 3-(tert-butyl-dimethyl-silanyloxy)-phenylamine (0.19 g, 0.84 mmol) and p-toluenesulfonic acid monohydrate (79.9 mg, 0.42 mmol) (Aldrich) in isopropanol (4 mL) was placed in a microwave reactor (SmithSynthesizer™). The reaction mixture was heated at 160° C. for 1 h. The reaction mixture was concentrated and purified by flash chromatography eluting with EtOAc/$CH_2Cl_2$ (5:95) to afford the product. (Yield 0.13 g, 59%).

Example 23

This example illustrates a method for producing 3-[3-(2,6-dichloro-phenyl)-1-methyl-1H-pyrimido[4,5-e][1,3,4]oxadiazin-7-ylamino]-phenol.

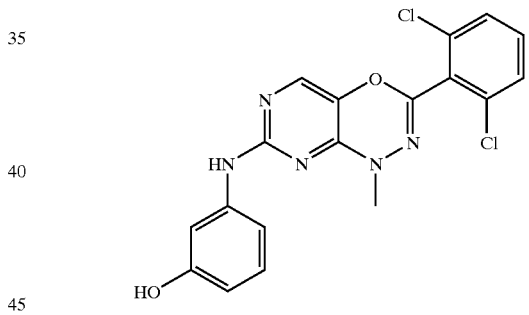

To a solution of [3-(tert-butyl-dimethyl-silanyloxy)-phenyl]-[3-(2,6-dichlorophenyl)-1-methyl-1H-pyrimido[4,5-e][1,3,4]oxadiazin-7-yl]-amine (0.13 g, 0.25 mmol) and tetrabutyl-ammonium fluoride (0.38 mL, 1.0 M solution in THF, 0.38 mmol) (Aldrich) in THF (5 mL) was stirred at room temperature for 18 h. It was concentrated and the residue was purified by flash chromatography eluting with EtOAc/$CH_2Cl_2$ (10:90) to obtain a solid. This solid was recrystallized from EtOAc/hexanes (1:1) to afford the product. (Yield 43.0 mg, 43%).

HRMS m/z Calculated for $C_{18}H_{13}Cl_2N_5O_2$ [(M+H)$^+$]: 402.0519. Found: 402.0523.

Example 24

This example illustrates a method for producing methanesulfonic acid 3-[3-(2,6-Dichloro-phenyl)-1-methyl-1H-pyrimido[4,5-e][1,3,4]oxadiazin-7-ylamino]-phenyl ester.

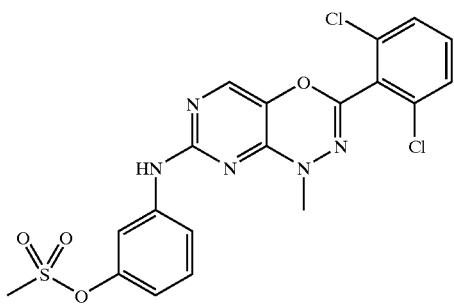

A solution of 3-[3-(2,6-dichloro-phenyl)-1-methyl-1H-pyrimido[4,5-e][1,3,4]oxadiazin-7-ylamino]-phenol (20.0 mg, 0.05 mmol), methanesulfonyl chloride (0.016 mL, 0.22 mmol) (Aldrich) and triethylamine (0.029 mL, 0.22 mmol) in CH$_2$Cl$_2$ (5 mL) was stirred at room temperature for 3 d. The reaction mixture was washed with water and brine, dried with MgSO$_4$, filtered and concentrated. The residue was purified by flash chromatography eluting with EtOAc/hexanes (2:3) to obtain a solid which was recrystallized from EtOAc/hexanes to afford the product. (Yield 11.6 mg, 48%).

HRMS m/z Calculated for C$_{19}$H$_{15}$Cl$_2$N$_5$O$_4$S [(M+H)$^+$]: 480.0295. Found: 480.0300.

Example 25

This example illustrates a method for producing 3-[3-(2,6-dichloro-phenyl)-1-methyl-1H-pyrimido[4,5-e][1,3,4]oxadiazin-7-ylamino]-N-methyl-benzamide.

Step 1. N-methyl-3-nitro-benzamide.

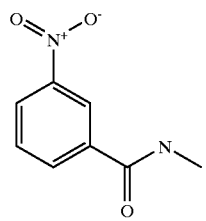

To a solution of 2 M methylamine in THF (100 mL) (Aldrich) and CHCl$_3$ (80 mL) at 0° C. was added 3-nitrobenzoylchloride (3 g, 16.17 mmol) (Fluka) in CHCl$_3$ (5 mL). The reaction mixture was stirred at 0° C. for 1 h. It was washed with water, 2 N HCl solution, sat. NaHCO$_3$ and brine, dried with MgSO$_4$, filtered and concentrated. The crude material was used in the next step without further purification. (Yield 2.47 g, 85%).

Step 2. N-Methyl-3-amino-benzamide.

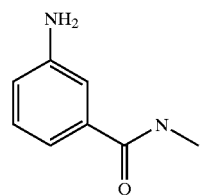

A mixture of N-methyl-3-nitro-benzamide (2.47 g, 13.71 mmol) and 10% Pd/C (0.5 g) in methanol (50 mL) was hydrogenated at room temperature and atmospheric pressure overnight. The reaction mixture was filtered through a Celite® pad and concentrated. The crude material was used in the next step without further purification. (Yield 2.06 g, 100%).

Step 3. 3-[3-(2,6-Dichloro-phenyl)-1-methyl-1H-pyrimido[4,5-e][1,3,4]oxadiazin-7-ylamino]-N-methyl-benzamide.

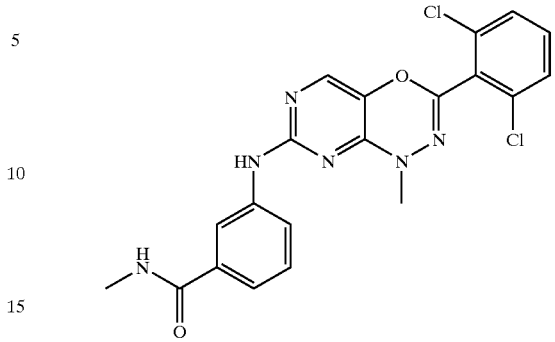

A solution of 7-methanesulfinyl-3-(2,6-dichloro-phenyl)-1-methyl-1H-pyrimido[4,5-e][1,3,4]oxadiazine (0.10 g, 0.28 mmol), N-methyl-3-amino-benzamide (84 mg, 0.56 mmol) and p-toluene acid monohydrate (53.3 mg, 0.28 mmol) (Aldrich) in isopropanol (4 mL) was placed in a microwave reactor (SmithSynthesizer™). The reaction mixture was heated at 170° C. for 1 h. The reaction mixture was concentrated and purified by RP-HPLC (C-18, eluting with MeCN/H$_2$O) to obtain a solid which was recrystallized from methanol to afford the product. (Yield 34 mg, 28%).

HRMS m/z Calculated for C$_{20}$H$_{16}$Cl$_2$N$_6$O$_2$ [(M+H)$^+$]: 443.0785. Found: 443.0791.

Example 26

This example illustrates a method for producing methyl-carbamic acid 3-[3-(2,6-dichloro-phenyl)-1-methyl-1H-pyrimido[4,5-e][1,3,4]oxadiazin-7-ylamino]-phenyl ester.

Step 1. Methyl-carbamic acid 3-nitro-phenyl ester.

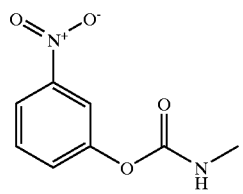

To a solution of 3-nitrophenol (3.0 g, 21.57 mmol) (Eastman) and triethylamine (3.01 mL, 21.57 mmol) in CH$_2$Cl$_2$ (40 mL) was added methyl isocyanate in CH$_2$Cl$_2$ (20 mL) (Aldrich). The reaction mixture was stirred at room temperature for 4 h. It was washed with 2N HCl and brine, dried with MgSO$_4$, filtered and concentrated. The crude material was recrystallized from methanol to afford the product. (Yield 3.01 g, 71%).

Step 2. Methyl-carbamic acid 3-amino-phenyl ester.

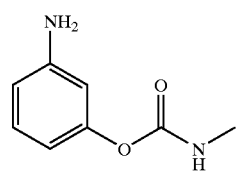

A mixture of methyl-carbamic acid 3-nitro-phenyl ester (3.01 g, 15.34 mmol) and 10% Pd/C (0.3 g) in methanol (50 mL) was hydrogenated at room temperature and atmospheric pressure overnight. The reaction mixture was filtered through a Celite® pad and concentrated. The residue was purified by flash chromatography eluting with EtOAc/hexanes (3:2) to afford the product. (Yield 1.66 g, 65%).

Step 3. Methyl-carbamic acid 3-[3-(2,6-dichloro-phenyl)-1-methyl-1H-pyrimido[4,5-e][1,3,4]oxadiazin-7-ylamino]-phenyl ester.

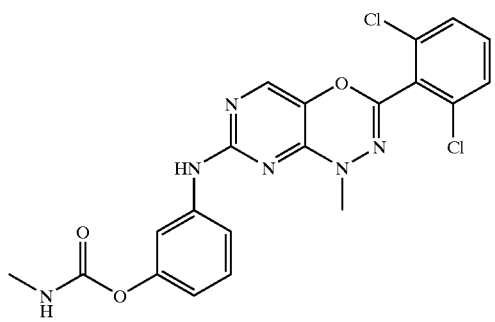

A solution of 7-methanesulfinyl-3-(2,6-dichloro-phenyl)-1-methyl-1H-pyrimido[4,5-e][1,3,4]oxadiazine (0.10 g, 0.28 mmol), methyl-carbamic acid 3-amino-phenyl ester (93 mg, 0.56 mmol) and p-toluenesulfonic acid monohydrate (53.3 mg, 0.28 mmol) (Aldrich) in isopropanol (4 mL) was placed in a microwave reactor (SmithSynthesizer™). The reaction mixture was heated at 170° C. for 1 h. The reaction mixture was concentrated and the residue purified by RP-HPLC (C-18, eluted with MeCN/H$_2$O) to obtain a solid which was recrystallized from methanol to afford the product. (Yield 43.5 mg, 33%).

HRMS m/z Calculated for $C_{20}H_{16}Cl_2N_6O_3$ [(M+H)$^+$]: 459.0734. Found: 459.0740.

Example 27

This example illustrates a method for producing 3,5-Dimethoxy-benzoic acid N'-(5-bromo-2-methylsulfanyl-pyrimidin-4-yl)-N'-methyl-hydrazide.

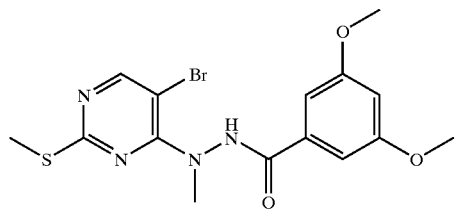

To a solution of N-(5-bromo-2-methylsulfanyl-pyrimidin-4-yl)-N-methyl-hydrazine (0.40 g, 1.61 mmol) and triethylamine (1.12 mL, 8.05 mmol) (Aldrich) in CH$_2$Cl$_2$ (15 mL) was added 3,5-dimethoxybenzoyl chloride (0.64 g, 3.21 mmol) (Aldrich). The reaction mixture was stirred at room temperature for 18 h. The precipitate was collected by filtration, washed with CH$_2$Cl$_2$ and dried to give the product. (Yield 0.49 g, 73%).

Example 28

This example illustrates a method for producing 3-(3,5-dimethoxy-phenyl)-1-methyl-7-methylsulfanyl-1H-pyrimido[4,5-e][1,3,4]oxadiazine.

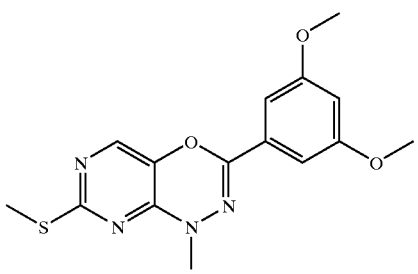

A mixture of 3,5-dimethoxybenzoic acid N'-(5-bromo-2-methylsulfanyl-pyrimidin-4-yl)-N'-methyl-hydrazide (0.49 g, 1.19 mmol), triethylamine (2.0 mL) and NaOH powder (50 mg, 1.25 mmol) in DMF (6 mL) was placed in a microwave reactor (SmithSynthesizer™). The reaction mixture was heated at 200° C. for 1.5 h. It was diluted with ethyl acetate and water. The organic layer was washed with brine, dried with MgSO$_4$, filtered and concentrated. The residue was purified by flash chromatography eluting with EtOAc/CH$_2$Cl$_2$ (5:95) to afford the product (Yield 0.21 g, 54%).

Example 29

This example illustrates a method for producing 7-methanesulfinyl-3-(3,5-dimethoxy-phenyl)-1-methyl-1H-pyrimido[4,5-e][1,3,4]oxadiazine.

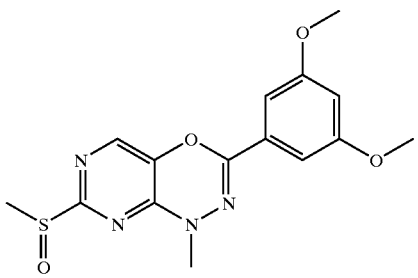

To a solution of 3-(3,5-dimethoxy-phenyl)-1-methyl-7-methylsulfanyl-1H-pyrimido[4,5-e][1,3,4]oxadiazine (0.21 g, 0.63 mmol) in THF (8 mL) at 0° C. was added Oxone® (0.54 g, 0.88 mmol) (Aldrich) in water (3 mL). The reaction mixture was stirred at 0° C. for 4 h and then diluted with CH$_2$Cl$_2$. The organic layer was washed with water and brine, dried with MgSO$_4$, filtered, concentrated and dried to give the product. (Yield 0.20 g, 91%).

Example 30

This example illustrates a method for producing [3-(3,5-dimethoxy-phenyl)-1-methyl-1H-pyrimido[4,5-e][1,3,4]oxadiazin-7-yl]-phenylamine.

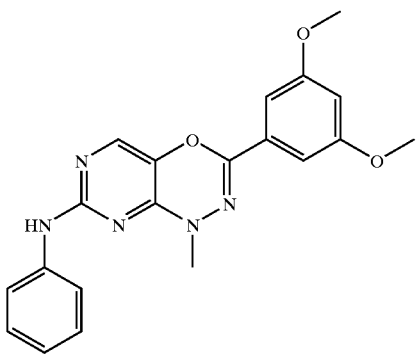

A mixture of 7-methanesulfinyl-3-(3,5-dimethoxy-phenyl)-1-methyl-1H-pyrimido[4,5-e][1,3,4]oxadiazine (0.10 g, 0.29 mmol) and aniline (2 mL) (Aldrich) was placed in a microwave reactor (SmithSynthesizer™). The reaction mixture was heated at 200° C. for 1 h. The precipitate was collected by filtration, washed with isopropanol and dried to give the product. (Yield 36 mg, 33%).

HRMS m/z Calculated for $C_{20}H_{19}N_5O_3$ [(M+H)$^+$]: 378.1561. Found: 378.1566.

Example 31

This example illustrates a method for producing [3-(3,5-dimethoxy-phenyl)-1-methyl-1H-pyrimido[4,5-e][1,3,4]oxadiazin-7-yl]-(4-fluoro-phenyl)-amine.

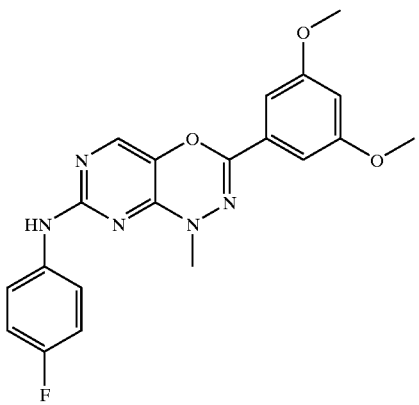

A mixture of 7-methanesulfinyl-3-(3,5-dimethoxy-phenyl)-1-methyl-1H-pyrimido[4,5-e][1,3,4]oxadiazine (0.10 g, 0.29 mmol) and p-fluoro-aniline (2 mL) (Acros) was placed in a microwave reactor (SmithSynthesizer™). The reaction mixture was heated at 200° C. for 1 h. The precipitate was collected by filtration, washed with isoprpoanol and dried to give the product. (Yield 24 mg, 22%).

HRMS m/z Calculated for $C_{20}H_{18}FN_5O_3$ [(M+H)$^+$]: 396.1467. Found: 396.1471.

Example 32

This example illustrates a method for producing 3-methoxy-benzoic acid N'-(5-bromo-2-methylsulfanyl-pyrimidin-4-yl)-N'-methyl-hydrazide.

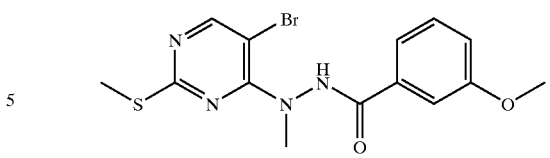

To a 0° C. solution of N-(5-bromo-2-methylsulfanyl-pyrimidin-4-yl)-N-methylhydrazine (0.40 g, 1.6 mmol) and triethylamine (0.45 mL, 3.23 mmol) in $CH_2Cl_2$ (30 mL) was added 3-methoxy-benzoyl chloride (0.25 mL, 1.78 mmol) (Aldrich). The reaction mixture was stirred at 0° C. for 3 h. The precipitate was collected by filtration, washed with $CH_2Cl_2$ and dried to give the product. (Yield 0.41 g, 66%).

Example 33

This example illustrates a method for producing 3-(3-methoxy-phenyl)-1-methyl-7-methylsulfanyl-1H-pyrimido[4,5-e][1,3,4]oxadiazine.

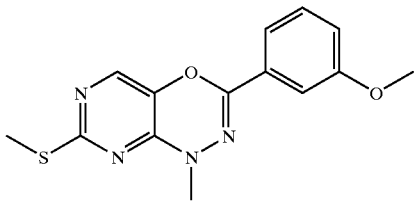

A mixture of 3-methoxy-benzoic acid N'-(5-bromo-2-methylsulfanyl-pyrimidin-4-yl)-N'-methyl-hydrazide (0.49 g, 1.28 mmol), triethylamine (2.0 mL) and NaOH powder (50 mg, 1.25 mmol) in DMF (4 mL) was placed in a microwave reactor (SmithSynthesizer™). The reaction mixture was heated at 200° C. for 1 h. It was diluted with ethyl acetate and water. The organic layer was washed with water and brine, dried with $MgSO_4$, filtered and concentrated. The residue was purified by flash chromatography eluting with EtOAc/$CH_2Cl_2$ (5:95) to afford the product. (Yield 0.38 g, 97%).

Example 34

This example illustrates a method for producing 7-methanesulfinyl-3-(3-methoxyphenyl)-1-methyl-1H-pyrimido[4,5-e][1,3,4]oxadiazine.

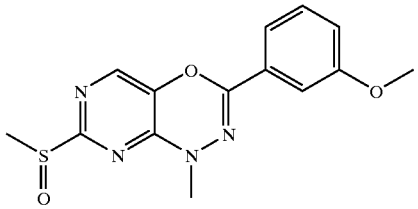

To a 0° C. solution of 3-(3-methoxy-phenyl)-1-methyl-7-methylsulfanyl-1H-pyrimido[4,5-e][1,3,4]oxadiazine (0.38 g, 1.26 mmol) in THF (12 mL) was added Oxone® (1.08 g, 1.76 mmol) (Aldrich) in water (6 mL). The reaction mixture was stirred at 0° C. for 4 h and then diluted with $CH_2Cl_2$. The organic layer was washed with water and brine, dried with $MgSO_4$, filtered and concentrated. The residue was washed with EtOAc and dried to give the product. (Yield 0.30 g, 75%).

Example 35

This example illustrates a method for producing [3-(3-methoxy-phenyl)-1-methyl-1H-pyrimido[4,5-e][1,3,4]oxadiazin-7-yl]-phenyl-amine.

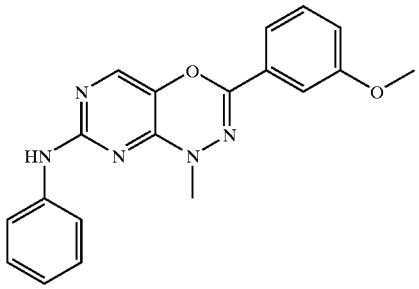

A mixture of 7-methanesulfinyl-3-(3-methoxy-phenyl)-1-methyl-1H-pyrimido[4,5-e][1,3,4]oxadiazine (0.15 g, 0.47 mmol) and aniline (2 mL) (Aldrich) was placed in a microwave reactor (SmithSynthesizer™). The reaction mixture was heated at 200° C. for 1 h. The mixture was concentrated and the precipitate was collected by filtration, washed with methanol and dried to give the product. (Yield 20 mg, 13%).

HRMS m/z Calculated for $C_{19}H_{17}N_5O_2$ [(M+H)$^+$]: 348.1455. Found: 348.1459.

Example 36

This example illustrates a method for producing [3-(3-methoxy-phenyl)-1-methyl-1H-pyrimido[4,5-e][1,3,4]oxadiazin-7-yl]-(4-fluoro-phenyl)-amine.

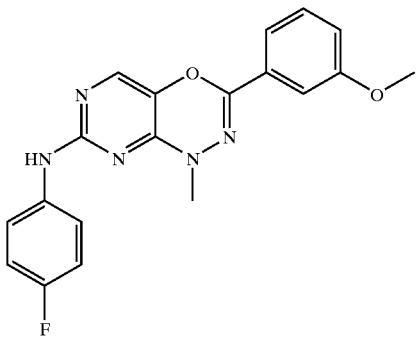

A mixture of 7-methanesulfinyl-3-(3-methoxy-phenyl)-1-methyl-1H-pyrimido[4,5-e][1,3,4]oxadiazine (0.15 g, 0.47 mmol) and p-fluoro-aniline (2 mL) (Acros) was placed in a microwave reactor (SmithSynthesizer™). The reaction mixture was heated at 200° C. for 1 h. The reaction mixture was concentrated and purified by RP-HPLC (C-18, eluting with MeCN/H$_2$O) to afford the product. (Yield 26 mg, 16%).

HRMS m/z Calculated for $C_{19}H_{16}FN_5O_2$ [(M+H)$^+$]: 366.1361. Found: 366.1365.

Example 37

This example illustrates a method for producing 2-chloro-5-methoxy-benzoic acid N'-(5-bromo-2-methylsulfanyl-pyrimidin-4-yl)-N'-methyl-hydrazide.

Step 1. 2-Chloro-5-methoxy-benzoic acid.

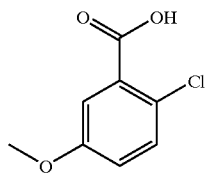

A solution of 4-chloro-3-methylanisole (3.0 g, 19.2 mmol) (Acros) and potassium permanganate (7.57 g, 47.9 mmol) in water (60 mL) was heated at reflux for 4 h. The precipitate was filtered and the solution was extracted with EtOAc. The aqueous phase was acidified with conc. HCl. The precipitate was collected by filtration, washed with water and dried to give the product. (Yield 0.78 g, 22%).

Step 2. 2-Chloro-5-methoxy-benzoyl chloride

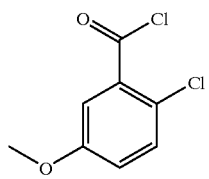

A solution of 2-chloro-5-methoxy-benzoic acid (0.78 g, 4.18 mmol) and thionyl chloride (0.4 mL, 5.43 mmol) (Aldrich) in CH$_2$Cl$_2$ (100 mL) was heated at reflux for 3 h. The reaction mixture was concentrated to give the product. (Yield 0.82 g, 95%).

Step 3. 2-Chloro-5-methoxy-benzoic acid N'-(5-bromo-2-methylsulfanyl-pyrimidin-4-yl)-N'-methyl-hydrazide.

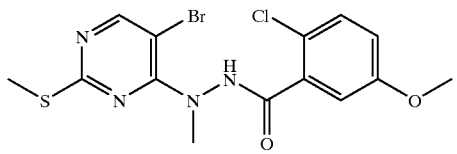

To a solution of N-(5-bromo-2-methylsulfanyl-pyrimidin-4-yl)-N-methyl-hydrazine (0.40 g, 1.61 mmol) and triethylamine (1.12 mL, 8.05 mmol) in CH$_2$Cl$_2$ (20 mL) was added 2-chloro-5-methoxy-benzoyl chloride (0.48 g, 2.34 mmol). The reaction mixture was stirred at room temperature for 18 h and then diluted with CH$_2$Cl$_2$. The organic layer was washed with water and brine, dried with MgSO$_4$, filtered and concentrated. The residue was purified by flash chromatography eluting with EtOAc/CH$_2$Cl$_2$ (5:95) to afford the product. (Yield 0.61 g, 91%).

Example 38

This example illustrates a method for producing 3-(2-chloro-5-methoxy-phenyl)-1-methyl-7-methylsulfanyl-1H-pyrimido[4,5-e][1,3,4]oxadiazine.

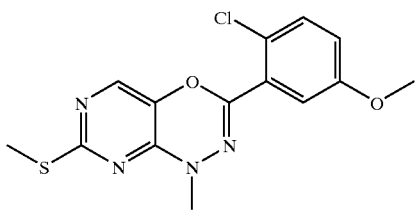

A solution of 2-chloro-5-methoxy-benzoic acid N'-(5-bromo-2-methylsulfanyl-pyrimidin-4-yl)-N'-methyl-hydrazide (0.61 g, 1.46 mmol), triethylamine (3.0 mL) and NaOH powder (100 mg, 2.5 mmol) in DMF (4 mL) was placed in a microwave reactor (SmithSynthesizer™). The reaction mixture was heated at 200° C. for 1.5 h and then diluted with ethyl acetate and water. The organic layer was washed with brine, dried with MgSO₄, filtered and concentrated. The residue was purified by flash chromatography eluting with EtOAc/CH₂Cl₂ (5:95) to afford the product. (Yield 0.30 g, 61%).

Example 39

This example illustrates a method for producing 7-methanesulfinyl-3-(2-chloro-5-methoxy-phenyl)-1-methyl-1H-pyrimido [4,5-e][1,3,4] oxadiazine.

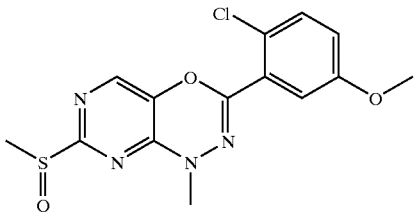

To a 0° C. solution of 3-(2-chloro-5-methoxy-phenyl)-1-methyl-7-methylsulfanyl-1H-pyrimido[4,5-e][1,3,4] oxadiazine (0.30 g, 0.89 mmol) in THF (10 mL) was added Oxone® (0.73 g, 1.19 mmol) (Aldrich) in water (6 mL). The reaction mixture was stirred at 0° C. for 4 h. and then diluted with CH₂Cl₂. The organic layer was washed with water and brine, dried with MgSO₄, filtered and concentrated to give the product. (Yield 0.30 g, 97%).

Example 40

This example illustrates a method for producing [3-(2-chloro-5-methoxy-phenyl)-1-methyl-1H-pyrimido[4,5-e][1,3,4]oxadiazin-7-yl]-phenylamine.

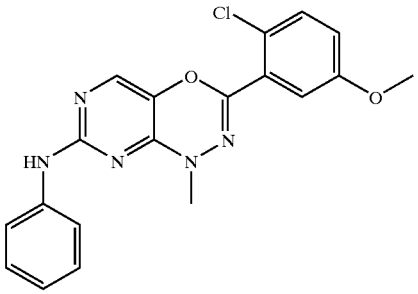

A mixture of 7-methanesulfinyl-3-(2-chloro-5-methoxy-phenyl)-1-methyl-1 H-pyrimido[4,5-e][1,3,4]oxadiazine (0.15 g, 0.42 mmol) and aniline (2 mL) (Aldrich) was placed in a microwave reactor (SmithSynthesizer™). The reaction mixture was heated at 200° C. for 1 h. The reaction mixture was concentrated. The precipitate was collected by filtration, washed with methanol and dried to give the product. (Yield 60 mg, 38%).

HRMS m/z Calculated for $C_{19}H_{16}ClN_5O_2$ [(M+H)⁺]: 382.1066. Found: 382.1072.

Example 41

This example illustrates a method for producing 2-methoxy-benzoic acid N'-(5-bromo-2-methylsulfanyl-pyrimidin-4-yl)-N'-methyl-hydrazide.

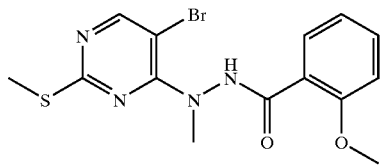

To a solution of N-(5-bromo-2-methylsulfanyl-pyrimidin-4-yl)-N-methyl-hydrazine (0.40 g, 1.61 mmol) and triethylamine (0.67 mL, 4.83 mmol) in CH₂Cl₂ (20 mL) was added 2-methoxy-benzoyl chloride (0.41 g, 2.41 mmol) (Eastman). The reaction mixture was stirred at room temperature for 18 h. The reaction mixture was washed with water and brine, dried with MgSO₄, filtered and concentrated. The residue was recrystallized from EtOAc/CH₂Cl₂ to afford the product. (Yield 0.45 g, 73%).

Example 42

This example illustrates a method for producing 3-(2-methoxy-phenyl)-1-methyl-7-methylsulfanyl-1H-pyrimido [4,5-e][1,3,4]oxadiazine.

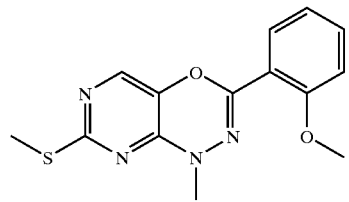

A mixture of 2-methoxy-benzoic acid N'-(5-bromo-2-methylsulfanyl-pyrimidin-4-yl)-N'-methyl-hydrazide (0.45 g, 1.17 mmol), triethylamine (2.0 mL) and NaOH powder (50 mg, 1.25 mmol) in DMF (8 mL) was placed in a microwave reactor (SmithSynthesizer™). The reaction mixture was heated at 200° C. for 1.5 h and then diluted with ethyl acetate and water. The organic layer was washed with brine, dried with MgSO₄, filtered and concentrated. The residue was purified by flash chromatography eluting with EtOAc/CH₂Cl₂ (5:95) to afford the product. (Yield 0.25 g, 71%).

Example 43

This example illustrates a method for producing 7-methanesulfinyl-3-(2-methoxy-phenyl)-1-methyl-1H-pyrimido[4,5-e][1,3,4]oxadiazine.

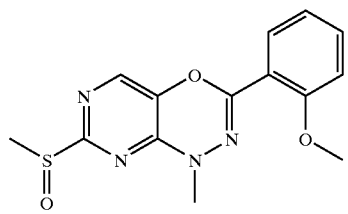

To a 0° C. solution of 3-(2-methoxy-phenyl)-1-methyl-7-methylsulfanyl-1H-pyrimido[4,5-e][1,3,4]oxadiazine (0.25 g, 0.83 mmol) in THF (10 mL) was added Oxone® (0.68 g, 1.11 mmol) (Aldrich) in water (3 mL). The reaction mixture was stirred at 0° C. for 3 h. and then diluted with CH$_2$Cl$_2$. The organic layer was washed with water and brine, dried with MgSO$_4$, filtered and concentrated. The residue was dried to give the product. (Yield 0.26 g, 100%).

Example 44

This example illustrates a method for producing [3-(2-methoxy-phenyl)-1-methyl-1H-pyrimido[4,5-e][1,3,4]oxadiazin-7-yl]-phenyl-amine.

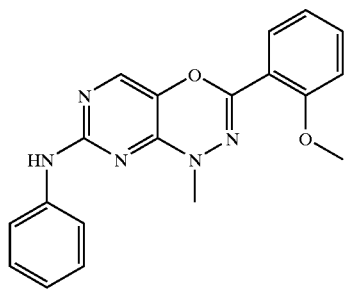

A mixture of 7-methanesulfinyl-3-(2-methoxy-phenyl)-1-methyl-1H-pyrimido[4,5-e][1,3,4]oxadiazine (0.10 g, 0.63 mmol) and aniline (2 mL) (Aldrich) was placed in a microwave reactor (SmithSynthesizer™). The reaction mixture was heated at 200° C. for 1 h. The reaction mixture was concentrated and purified by RP-HPLC (C-18, eluting with MeCN/H$_2$O) to afford the product. (Yield 23 mg, 16%).

HRMS m/z Calculated for C$_{19}$H$_{17}$N$_5$O$_2$ [(M+H)$^+$]: 348.1455. Found: 348.1458.

Example 45

This example illustrates a method for producing 2,6-Difluoro-benzoic acid N'-(5-bromo-2-methylsulfanyl-pyrimidin-4-yl)-N'-methyl-hydrazide.

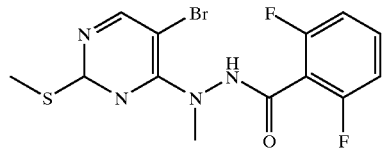

To a 0° C. solution of N-(5-bromo-2-methylsulfanyl-pyrimidin-4-yl)-N-methyl-hydrazine (0.40 g, 1.61 mmol) and triethylamine (0.49 mL, 3.51 mmol) in CH$_2$Cl$_2$ (20 mL) was added 2,6-difluorobenzoyl chloride (0.23 mL, 1.79 mmol) (Apollo-Chem.). The reaction mixture was stirred at 0° C. for 30 minutes and then washed with water and brine, dried with MgSO$_4$, filtered and concentrated. The residue was recrystallized from EtOAc/CH$_2$Cl$_2$ to afford the product. (Yield 0.25 g, 40%).

Example 46

This example illustrates a method for producing 3-(2,6-difluorophenyl)-1-methyl-7-methylsulfanyl-1H-pyrimido[4,5-e][1,3,4]oxadiazine.

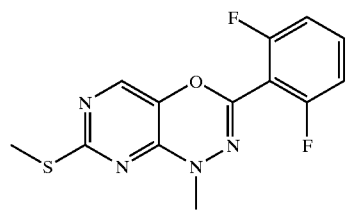

A mixture of 2,6-difluorobenzoic acid N'-(5-bromo-2-methylsulfanyl-pyrimidin-4-yl)-N'-methyl-hydrazide (0.25 g, 0.64 mmol), triethylamine (3.0 mL) and NaOH powder (50 mg, 1.3 mmol) in MeCN (4 mL) was placed in a microwave reactor (SmithSynthesizer™). The reaction mixture was heated at 160° C. for 1 h. The solid was filtered and the solution was concentrated. The residue was purified by flash chromatography eluting with EtOAc/CH$_2$Cl$_2$ (1:99) to afford the product. (Yield 0.11 g, 55%).

Example 47

This example illustrates a method for producing 7-methanesulfinyl-3-(2,6-difluorophenyl)-1-methyl-1H-pyrimido[4,5-e][1,3,4]oxadiazine.

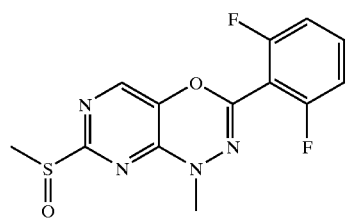

To a 0° C. solution of 3-(2,6-difluorophenyl)-1-methyl-7-methylsulfanyl-1H-pyrimido[4,5-e][1,3,4]oxadiazine (0.11 g, 0.36 mmol) in THF (5 mL) was added Oxone® (0.29 g, 0.48 mmol) (Aldrich) in water (3 mL). The reaction mixture was stirred at 0° C. for 3 h. and then diluted with CH$_2$Cl$_2$. The organic layer was washed with water and brine, dried with MgSO$_4$, filtered and concentrated. The residue was dried to give the product. (Yield 0.10 g, 83%).

Example 48

This example illustrates a method for producing [3-(2,6-difluoro-phenyl)-1-methyl-1H-pyrimido[4,5-e][1,3,4]oxadiazin-7-yl]-phenyl-amine.

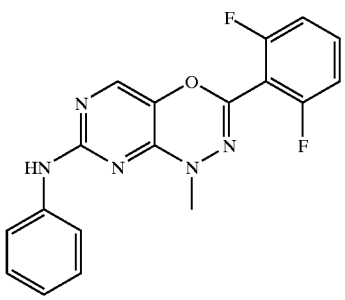

A mixture of 7-methanesulfinyl-3-(2,6-difluoro-phenyl)-1-methyl-1H-pyrimido[4,5-e][1,3,4]oxadiazine (0.10 g, 0.31 mmol) and aniline (2 mL) (Aldrich) was placed in a microwave reactor (SmithSynthesizer™). The reaction mixture was heated at 200° C. for 1 h. The reaction mixture was concentrated and the precipitate was collected by filtration, washed with methanol and dried to give the product. (Yield 68 mg, 62%).

HRMS m/z Calculated for $C_{18}H_{13}F_2N_5O$ [(M+H)$^+$]: 353.1088. Found: 353.1088.

Example 49

This example illustrates a method for producing 2,4-Difluoro-benzoic acid N'-(5-bromo-2-methylsulfanyl-pyrimidin-4-yl)-N'-methyl-hydrazide.

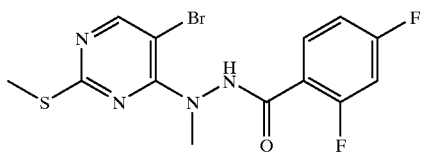

To a 0° C. solution of N-(5-bromo-2-methylsulfanyl-pyrimidin-4-yl)-N-methyl-hydrazine (0.40 g, 1.61 mmol) and triethylamine (0.49 mL, 3.51 mmol) in $CH_2Cl_2$ (20 mL) was added 2,4-difluorobenzoyl chloride (0.22 mL, 1.79 mmol) (Aldrich). The reaction mixture was stirred at 0° C. for 30 minutes and then washed with water and brine, dried with $MgSO_4$, filtered and concentrated. The residue was recrystallized from EtOAc/$CH_2Cl_2$ to afford the product. (Yield 0.41 g, 65%).

Example 50

This example illustrates a method for producing 3-(2,4-difluorophenyl)-1-methyl-7-methylsulfanyl-1H-pyrimido[4,5-e][1,3,4]oxadiazine.

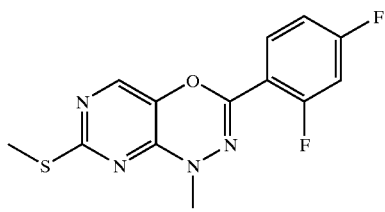

A mixture of 2,4-difluoro-benzoic acid N'-(5-bromo-2-methylsulfanyl-pyrimidin-4-yl)-N'-methyl-hydrazide (0.24 g, 0.62 mmol), triethylamine (3.0 mL) and NaOH powder (50 mg, 1.3 mmol) in MeCN (4 mL) was placed in a microwave reactor (SmithSynthesizer™). The reaction mixture was heated at 160° C. for 1 h. The solid was filtered and the solution was concentrated. The residue was purified by flash chromatography eluting with EtOAc/$CH_2Cl_2$ (1:99) to afford the product. (Yield 0.15 g, 79%).

Example 51

This example illustrates a method for producing 7-methanesulfinyl-3-(2,4-difluoro-phenyl)-1-methyl-1H-pyrimido [4,5-e][1,3,4]oxadiazine.

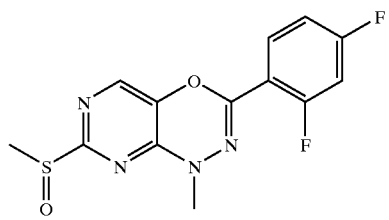

To a 0° C. solution of 3-(2,4-difluorophenyl)-1-methyl-7-methylsulfanyl-1H-pyrimido[4,5-e][1,3,4]oxadiazine (0.15 g, 0.49 mmol) in THF (10 mL) was added Oxone® (0.40 g, 0.65 mmol) (Aldrich) in water (4 mL). The reaction mixture was stirred at 0° C. for 3 h. and then diluted with $CH_2Cl_2$. The organic layer was washed with water and brine, dried with $MgSO_4$, filtered and concentrated. The residue was dried to give the product. (Yield 0.15 g, 94%).

Example 52

This example illustrates a method for producing [3-(2,4-difluoro-phenyl)-1-methyl-1H-pyrimido[4,5-e][1,3,4]oxadiazin-7-yl]-phenyl-amine.

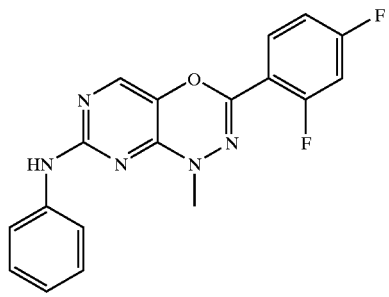

A mixture of 7-methanesulfinyl-3-(2,6-difluoro-phenyl)-1-methyl-1H-pyrimido[4,5-e][1,3,4]oxadiazine (0.10 g, 0.31 mmol) and aniline (1 mL) (Aldrich) were placed in a microwave reactor (SmithSynthesizer™). The reaction mixture was heated at 200° C. for 1 h. The reaction mixture was concentrated and purified by RP-HPLC (C-18, eluting with MeCN/$H_2O$) to afford the product. (Yield 46 mg, 42%).

HRMS m/z Calculated for $C_{18}H_{13}F_2N_5O$ [(M+H)$^+$]: 353.1088. Found: 353.1092.

Example 53

This example illustrates a method for producing [3-fluoro-2-(1-methyl-7-methylsulfanyl-1H-pyrimido[4,5-e][1,3,4]oxadiazin-3-yl)-phenyl]-dimethyl-amine.

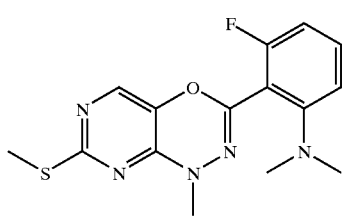

To a mixture of 2,6-difluoro-benzoic acid N'-(5-bromo-2-methylsulfanyl-pyrimidin-4-yl)-N'-methyl-hydrazide (0.36 g, 0.92 mmol), triethylamine (2.0 mL) and NaOH powder (50 mg, 1.3 mmol) in DMF (4 mL) was placed in a microwave reactor (SmithSynthesizer™). The reaction mixture was heated at 200° C. for 1.5 h. and then diluted with ethyl acetate and water. The organic layer was washed with water and brine, dried with MgSO$_4$, filtered and concentrated. The residue was purified by flash chromatography eluting with EtOAc/CH$_2$Cl$_2$ (5:95) to afford the product. (Yield 0.29 g, 94%).

Example 54

This example illustrates a method for producing [3-fluoro-2-(7-methanesulfinyl-1 methyl-1-H-pyrimido[4,5-e][1,3,4]oxadiazin-3-yl)-phenyl]-dimethyl-amine.

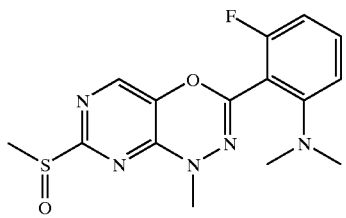

To a solution of [3-fluoro-2-(1-methyl-7-methylsulfanyl-1H-pyrimido[4,5-e][1,3,4]oxadiazin-3-yl)-phenyl]-dimethyl-amine (0.29 g, 0.87 mmol) in THF (10 mL) at 0° C. was added Oxone® (0.77 g, 1.26 mmol) (Aldrich) in water (4 mL). The reaction mixture was stirred at 0° C. for 4 h. and then diluted with CH$_2$Cl$_2$. The organic layer was washed with water and brine, dried with MgSO$_4$, filtered and concentrated. The residue was dried to give the product. (Yield 0.14 g, 47%).

Example 55

This example illustrates a method for producing [3-(2-dimethylamino-6-fluoro-phenyl)-1-methyl-1H-pyrimido[4,5-e][1,3,4]oxadia-zin-7-yl]-phenyl-amine.

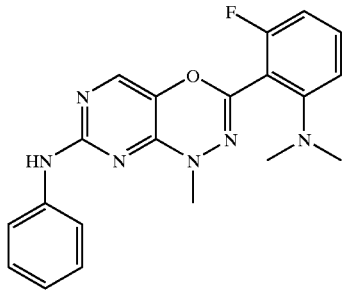

A mixture of [3-fluoro-2-(7-methanesulfinyl-1-methyl-1H-pyrimido[4,5-e-][1,3,4]oxadiazin-3-yl)-phenyl]-dimethyl-amine (80.0 mg, 0.31 mmol) and aniline (2 mL) (Aldrich) was placed in a microwave reactor (SmithSynthesizer™). The reaction mixture was heated at 200° C. for 1 h. The reaction mixture was concentrated and the residue was purified by RP-HPLC (C-18, eluting with MeCN/H$_2$O) to afford the product. (Yield 36 mg, 42%).

HRMS m/z Calculated for $C_{20}H_{19}FN_6O$ [(M+H)$^+$]: 379.1677. Found: 379.1680.

Example 56

This example illustrates a various representative pharmaceutical formulations containing a compound of Formula (I).

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

All of the above ingredients, except water, are combined and heated to 60–70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| compound of the invention | 500 mg |
|---|---|
| Witepsol ® H-15 | balance |

Example 57

This example illustrates an in vitro assay procedure for determining p38 MAP kinase inhibition by a compound of Formula I.

The p-38 MAP kinase inhibitory activity of compounds of this invention in vitro is determined by measuring the transfer of the γ-phosphate from γ-$^{33}$P-ATP by p-38 kinase to Myelin Basic Protein (MBP), using the a minor modification of the method described in Ahn, N. G.; et al. *J. Biol. Chem.* Vol. 266(7), 4220–4227, (1991).

The phosphorylated form of the recombinant p38 MAP kinase was expressed with SEK-1 and MEKK in *E. Coli* and then purified by affinity chromatography using a Nickel column.

The phosphorylated p38 MAP kinase is diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium vanadate, 1 mM dithiothreitol, 40 mM magnesium chloride). Test compound dissolved in DMSO or only DMSO (control) is added and the samples are incubated for 10 min at 30° C. The kinase reaction is initiated by the addition of a substrate cocktail containing MBP and γ-$^{33}$P-ATP. After incubating for an additional 20 min at 30° C., the reaction is terminated by adding 0.75% phosphoric acid. The phosphorylated MBP is then separated from the residual γ-$^{33}$P-ATP using a phosphocellulose membrane (Millipore, Bedford, Mass.) and quantitated using a scintillation counter (Packard, Meriden, Conn.).

Compounds of the invention are active in this assay. The p-38 inhibitory activities (expressed as $IC_{50}$, the concentration causing 50% inhibition of the p-38 enzyme being assayed) of some compounds of the invention are:

| Cpd # | $IC_{50}$, μM |
|---|---|
| 1 | 0.189 |
| 2 | 2.2 |

Example 58

This examples illustrates an in vitro assay procedure for determining inhibition of LPS-induced TNF-α production in THP1 cells.

The ability of the compounds of this invention to inhibit the TNF-α release is determined using aminor modification of the methods described in described in Blifeld, C. et al. *Transplantation*, Vol. 51(2), 498–503, (1991).

Induction of TNF Biosynthesis:

THP-1 cells are suspended in culture medium [RPMI (Gibco-BRL, Gailthersburg, Md.) containing 15% fetal bovine serum, 0.02 mM 2-mercaptoethanol], at a concentration of $2.5 \times 10^6$ cells/ml and then plated in 96 well plate (0.2 ml aliquots in each well). Test compounds are dissolved in DMSO and then diluted with the culture medium such that the final DMSO concentration is 5%. 20 μl aliquots of test solution or only medium with DMSO (control) are added to each well. The cells are incubated for 30 min., at 37° C. LPS (Sigma, St. Louis, Mo.) was added to the wells at a final concentration of 0.5 μg/ml, and cells are incubated for an additional 2 h. At the end of the incubation period, culture supernatants are collected and the amount of TNF-α present is determined using an ELISA assay as described below.

ELISA Assay:

The amount of human TNF-α present is determined by a specific trapping ELISA assay using two anti-TNF-α antibodies (2TNF-H22 and 2TNF-H34) described in Reimund, J. M., et al. *GUT*. Vol. 39(5), 684–689 (1996).

Polystyrene 96-well plates are coated with 50 μl per well of antibody 2TNF-H22 in PBS (10 μg/ml) and incubated in a humidified chamber at 4° C. overnight. The plates are washed with PBS and then blocked with 5% nonfat-dry milk in PBS for 1 hour at room temperature and washed with 0.1% BSA (bovine serum albumin) in PBS.

TNF standards are prepared from a stock solution of human recombinant TNF-α (R&D Systems, Minneapolis, Minn.). The concentration of the standards in the assay begin at 10 ng/ml followed by 6 half log serial dilution's.

25 μl aliquots of the above culture supernatants or TNF standards or only medium (control) are mixed with 25 μl aliquots of biotinylated monoclonal antibody 2TNF-H34 (2 μg/ml in PBS containing 0.1% BSA) and then added to each well. The samples are incubated for 2 h at room temperature with gentle shaking and then washed 3 times with 0.1% BSA in PBS. 50 μl of peroxidase-streptavidin (Zymed, S. San Francisco, Calif.) solution containing 0.416 μg/ml of peroxidase-streptavidin and 0.1% BSA in PBS is added to each well. The samples were incubated for an additional 1 h at room temperature and then washed 4 times with 0.1% BSA in PBS. 50 μl of O-phenylenediamine solution (1 μg/ml O-phenylene-diamine and 0.03% hydrogen peroxide in 0.2M citrate buffer pH 4.5) is added to each well and the samples were incubated in the dark for 30 min., at room temperature. Optical density of the sample and the reference are read at 450 nm and 650 μm, respectively. TNF-α levels are determined from a graph relating the optical density at 450 nm to the concentration used.

The $IC_{50}$ value is defined as the concentration of the test compound corresponding to half-maximal reduction in 450 nm absorbance.

Example 59

This examples illustrates an in vio assay procedure for determining inhibition of LPS-induced TNF-α production in rats.

The ability of the compounds of this invention to inhibit the TNF-α release, in vivo, is determined using aminor modification of the methods described in described in Zanetti, G.; Heumann, D., et. al., "Cytokine production after intravenous or peritoneal Gram-negative bacterial challenge in mice," *J. Immunol.*, 148, 1890, (1992) and Sekut, L., Menius, J. A., et. al., "Evaluation of the significance of elevated levels of systemic and localized tumor necrosis factor in different animal models of inflammation," *J. Lab. Clin. Med.*, 124, 813, (1994).

Female Sprague-Dawley rats weighing 110–140 grams (Charles River, Hollister, Calif.) are acclimated for one week. Groups containing 8 mice each were dosed orally either with the test compounds dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 min., the mice are injected intraperitoneally with 50 μg/kg of LPS (Sigma, St. Louis, Mo.). After 1.5 h, the mice are sacrificed by $CO_2$ inhalation and blood was harvested by cardiocentesis. Blood is clarified by centrifugation at 15,600×g for 5 min., and sera were transferred to clean tubes and frozen at −20° C. until analyzed for TNF-α by ELISA assay (Biosource International, Camarillo, Calif.) following the manufacturer's protocol.

Example 60

This examples illustrates an in vivo adjuvant arthritis assay in rats.

The Anti-inflammatory activity of the compounds of this invention is determined utilizing adjuvant induced arthritis in rats. Briefly, Female Sprague Dawley rats, weighing 120–155 g (Charles River, Hollister, Calif.) are acclimated in-house for approximately 1 week prior to use. On day 1, the animals were injected intradermally in the ¼ proximal portion of the tail with 0.1 ml of a mineral oil (Sigma, St. Louis, Mo.) suspension of heat killed and dried *Mycobacterium Butyricum* (Difco, Bacto., Des., Lot 115979JA/EXP9/99) at a concentration of 1 mg/0.1 ml.

On day 7, the test compounds are administered in CMC vehicle through to day 18. On day 18, following the administration of the compound, animals were weighed. Clinical scores are obtained to evaluate the intensity of edema in the four paws and tail. A score of 0 to 4 is assigned to each paw and 0 to 3 to the tail such that the maximum score is 19. Polyarthritic animals are scored 0 when no inflammatory signs (swelling and redness) were observed in any of the small joints (intraphalangeal, metacarpophalangeal, metatarsophalangeal) or large joints (wrist/carpus, ankle/tarsus). Animals are scored 1 when slight inflammation was observed, 2 moderate edema, 3 severe edema, and 4 when very severe edema was present. The tail is scored 0 when no signs of edema or necrotic tissue was observed, 1 when inocula injection sites and immediate surrounding tissue exhibit slight edema, 2 when approximately ¼ of the tail was either inflamed or exhibiting necrotic tissue, and 3 when over ¼ of the tail exhibited severe necroses or edema. Following clinical scores, the hind paws are transected at the distal tibia, just proximal to the tarsal joint. The left and right hind paws are weighed individually, and recorded.

Example 61

This examples demonstrates an in vitro assay procedure for determining FGFR kinase inhibition.

To determine inhibition of FGFR activity, kinase assays were conducted using an HTRF (Homogeneous Time Resolved Fluorescence) assay. This assay is described in A. J. Kolb et. al., Drug Discovery Today, 1998, 3(7), p 333.

Prior to kinase reaction, recombinant GST-tagged FGFR enzyme was activated at room temperature for 1 hour in the following activation buffer: 100 mM HEPES, pH 7.4, 50 mM NaCl, 20 mM $MgCl_2$, and 4 mM ATP.

Kinase activity assays were performed in 96-well polypropylene plates (Falcon) with a total volume of 90 μL in each well. Each well contained 1 μM substrate (Biotin-EEEEYFELV), 1.5 μM activated FGFR, and a test compound with one of 8 assay concentrations ranging from 100 μM to 128 pM (1:5 serial dilution). The kinase activity assay was done in the presence of 100 mM HEPES, pH 7.4, 1 mM DTT, 0.1 mM $Na_2VO_4$, 0.4 mM $MgCl_2$, 0.4 mM $MnCl_2$, 50 mM NaCl (from KDR stock solution), 1% DMSO (from compound), 10 μM ATP ($K_m$=8.5 μM for FGFR) and 0.02% BSA. The reaction was incubated at 37° C. for 30 minutes. To stop the FGFR reaction, 72 μL of reaction mixture was transferred into a STOP plate containing 18 μL of revelation buffer (20 mM EDTA, 50 mM HEPES, pH 7.4, 0.02% BSA, 10 nM Eu-labelled anti-p Y antibody (final conc. 2 nM), and 100 nM streptavidin (final conc. 20 nM)). After mixing, 35 μL of solution was transferred into duplicate wells of a 384-well black plate (Costar), and read at 615/665 nm on a Wallac Victor 5 reader.

Compound $IC_{50}$ values were determined from duplicate sets of data, and calculated by using Excel and fitting data to equation Y=[(a−b)/{1+(X/c)$^d$}]+b, where a and b are enzyme activity in the presence of no test inhibitor compound and an infinite amount of inhibitor test compound, respectively, c is the $IC_{50}$ and d is the hill constant of the compound response. The $IC_{50}$ value is the concentration of test compound that reduces by 50% the enzyme activity under the test conditions described. Compounds of the invention were active in the assay. Selected $IC_{50}$ values are shown below.

| Cpd. No. | $IC_{50}$ μM |
|---|---|
| 5 | 0.18 |
| 6 | 0.24 |
| 7 | 0.32 |

Example 62

This example illustrates the synthesis of [3-(2-bromophenyl)-1-methyl-1H-pyrimido[4,5-e][1,3,4]oxadiazin-7-yl]-(3-methanesulfinylphenyl)amine using the method described under Scheme 1.

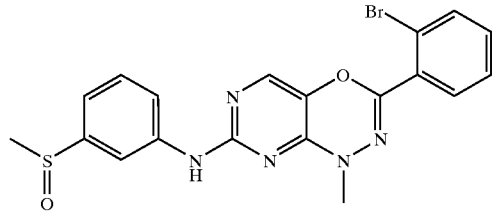

Step 1: preparation of 5-bromo-4-(1-methylhydrazino)-2-methylthiopyrimidine.

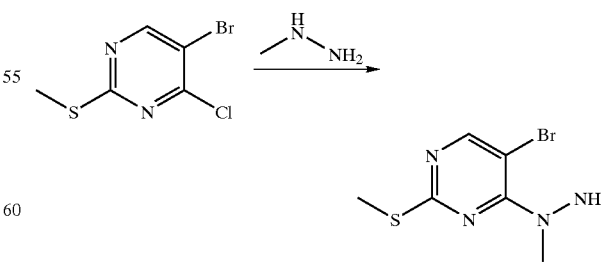

To 5-Bromo-4-(1-methylhydrazino)-2-methylthiopyrimidine (19.798 g, 82.66 mmol) (Barrett, H. W.; Goodman, I; Ditter, K, *J. Am. Chem. Soc*, 1948 70:1753) in 180 mL of dichloromethane at 0° C. was added methyl hydrazine with stirring. After addition was complete, the resulting mixture was stirred from 0° C. to room temperature for 2 hours. By TLC the reaction was then complete. The mixture was added to ethyl acetate and washed with water twice, and finally washed with brine. The organic layer was dried over magnesium sulfate, filtered and concentrated to give the product as a white solid (20 g, (M+H)⁺=249).

Step 2. Preparation of 2-bromobenzoic acid N'-(5-bromo-2-methylsulfanyl-pyrimidin-4-yl)-N'-methyl-hydrazide

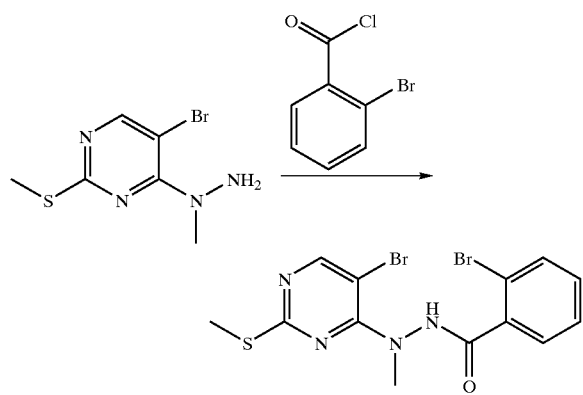

To 5-Bromo-4-(1-methylhydrazino)-2-methylthiopyrimidine (5.238 g, 21.03 mmol) and triethylamine (5.8 mL, 2.0 Eq) in dichloromethane (100 mL) at 0° C. was added 2-bromobenzoyl chloride (3 mL, 2.0 Eq), and the resulting mixture was stirred from 0° C. to room temperature overnight. By TLC, the reaction was not complete, so additional 2-bromobenzoyl chloride (0.5 mL) was added and the mixture was stirred another 4 hours. The reaction was complete by TLC at this point. A white solid was collected by filtration, washed with cold diethyl ether and then dried to give the title compound as a white solid (7 g, (M+H)⁺=432).

Step 3. Preparation of 3-(2-bromophenyl)-1-methyl-7-methylsulfanyl-1H-pyrimido[4,5-e][1,3,4]-oxadiazine.

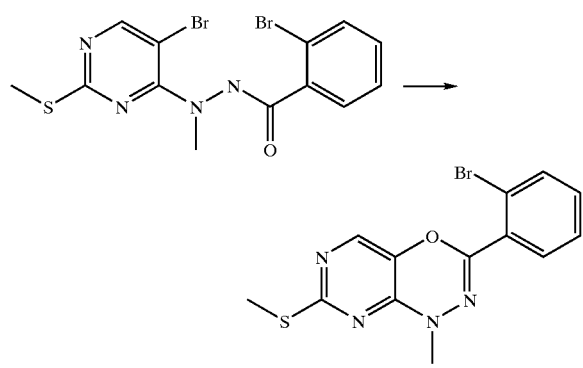

2-Bromobenzoic acid N'-(5-bromo-2-methylsulfanyl-pyrimidin-4-yl)-N'-methyl-hydrazide (3.0 g, 6.94 mmol), triethylamine (9.7 mL, 1.0 Eq), dimethylformamide (70 mL) and sodium hydroxide (1.4 g, 5 Eq) were mixed together and heated at 110° C. for 1 hour. Then the mixture was cooled to room temperature, diluted with ethyl acetate (1000 mL) and washed with water (1×150 mL) followed by Brine (1×150 mL) to provide 1 g of crude product. The crude material was purified by flash column chromatography, eluting on 22 g of Silica Gel 60 (230–400 mesh) with 5% ethyl acetate in hexanes to give the title compound as a white powder (251 mg, (M+H)⁺=353).

Step 4. Preparation of 3-(2-bromophenyl)-7-methanesulfonyl-1-methyl-1H-pyrimido[4,5-e][1,3,4]-oxadiazine.

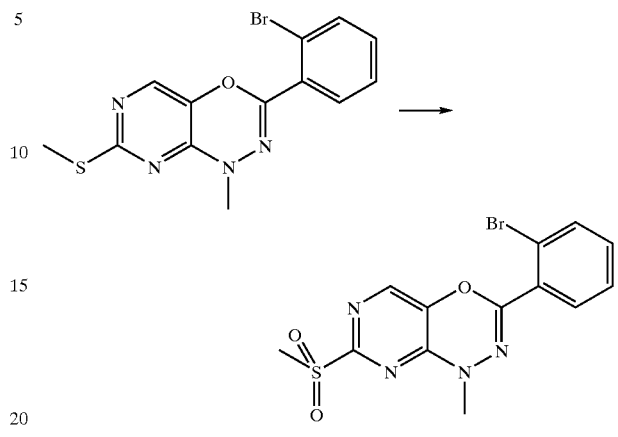

3-(2-Bromophenyl)-1-methyl-7-methylsulfanyl-1H-pyrimido[4,5-e][1,3,4]oxadiazine (468 mg, 1.33 mmol) was dissolved in tetrahydrofuran (10 mL) with stirring at 0° C., and a solution of Oxone (Aldrich, 2.016 g, 2.5 Eq) in water (10 mL) was added. The mixture was stirred from 0° C. to room temperature overnight. The next day the reaction was complete as confirmed by TLC. The mixture was added to ethyl acetate (85 mL) and washed with water (3×25 mL) followed by Brine (1×25 mL). The ethyl acetate layer was dried over magnesium sulfate, filtered and concentrated to give the title compound as a slightly yellow powder (489 mg, (M+H)⁺=384).

Step 5. Preparation of [3-(2-bromophenyl)-1-methyl-1H-pyrimido[4,5-e][1,3,4]oxadiazin-7-yl]-(3-methylsulfanyl-phenyl)amine.

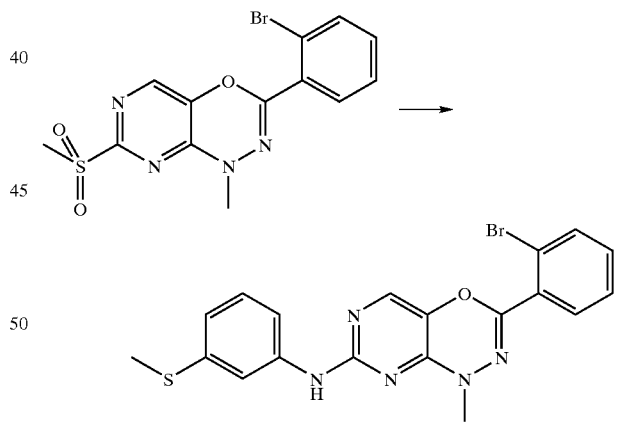

3-(2-Bromophenyl)-7-methanesulfonyl-1-methyl-1H-pyrimido[4,5-e][1,3,4]-oxadiazine (379 mg, 0.99 mmol) and 3-methylsulfanyl-phenylamine (Aldrich, 1.342 g, 10 Eq) were mixed together and heated with stirring at 140° C. for 1 hour. After TLC analysis confirmed that the reaction was complete, it was cooled to room temperature. Purification was by flash column chromatography on Silica Gel 60, eluting first with 5% ethyl acetate in hexanes (to remove the aniline), then with 50% ethyl acetate in hexanes, and finally with 2% methanol in dichloromethane to give the title compound as a slightly yellow solid (109 mg, (M+H)⁺=443).

Step 6. Preparation of [3-(2-bromophenyl)-1-methyl-1H-pyrimido[4,5-e][1,3,4]oxadiazin-7-yl]-(3-methanesulfinyl-phenyl)amine

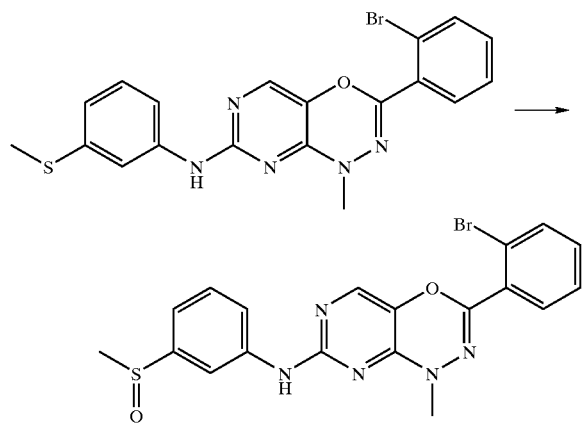

[3-(2-bromophenyl)-1-methyl-1H-pyrimido[4,5-e][1,3,4]oxadiazin-7-yl]-(3-methylsulfanyl-phenyl)-amine (109 mg, 0.25 mmol) was taken up in tetrahydrofuran (2.5 mL), and a solution of Oxone (Aldrich, 158 mg, 1.04 Eq) in water (2.5 mL) was added dropwise with stirring at 0° C. After stirring at 0° C. for 60 minutes, the reaction was complete. To the reaction mixture was added ethyl acetate and water, and the mixture partitioned and the layers separated. Then the organic layer was washed with additional water 2x, and finally washed with brine. The ethyl acetate layer was dried over magnesium sulfate, filtered and concentrated to give the crude product. This was purified by preparative TLC, eluting with 50% ethyl acetate in hexanes to give the title compound (66 mg, (M+H)$^+$=460).

Example 63

This example illustrates a method for producing [3-(2-bromophenyl)-1-methyl-1H-pyrimido[4,5-e][1,3,4]oxadiazin-7-yl]-(4-morpholin-4-yl-phenyl)amine.

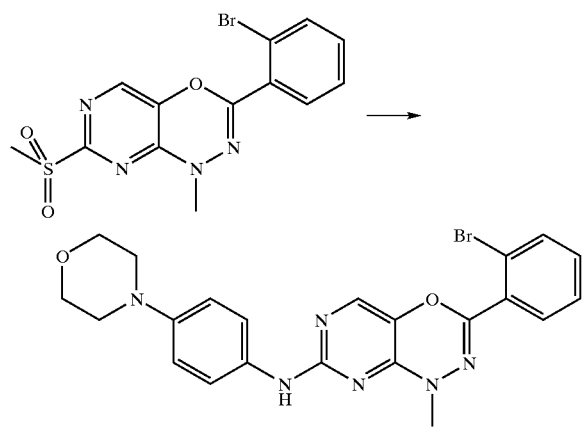

3-(2-Bromophenyl)-7-methanesulfonyl-1-methyl-1H-pyrimido[4,5-e][1,3,4]oxadiazine (108 mg, 0.28 mmol) and N-(4-aminophenyl)morpholine (Aldrich, 265 mg, 5.3 Eq) were mixed together and heated at 140° C. for 1 hour. The mixture was then cooled to room temperature and the crude product purified by preparative TLC, eluting with 50% ethyl acetate in hexanes to give the title compound as a slightly yellow powder (76 mg, (M+H)$^+$=482).

Example 64

This example illustrates a method for producing [3-(2,6-dichlorophenyl)-1-methyl-1H-pyrimido[4,5-e][1,3,4]oxadiazin-7-yl]-(4-morpholin-4-yl-phenyl)amine.

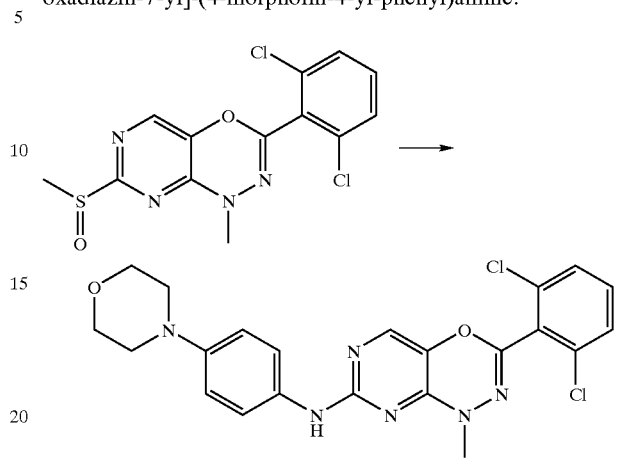

3-(2,6-Dichlorophenyl)-7-methanesulfinyl-1-methyl-1H-pyrimido[4,5-e][1,3,4]-oxadiazine (166 mg, 0.46 mmol) and N-(4-aminophenyl)morpholine (Aldrich, 811 mg, 10.0 Eq) were mixed together and heated at 135° C. for 3.5 hours. By TLC, the reaction was then complete, and the reaction mixture was cooled to room temperature. The crude product was purified by preparative TLC, eluting with 50% ethyl acetate in hexanes to give the title compound as a yellowish powder (148 mg, (M+H)$^+$=471, m.p.=192.2–200.3° C.).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety for all purposes.

What is claimed is:

1. A compound of the formula:

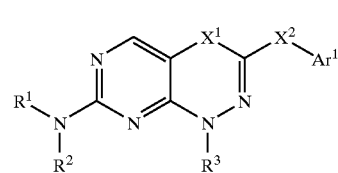

I or a pharmaceutically acceptable salt thereof, wherein

R$^1$ is hydrogen or alkyl;

R$^2$ is alkyl, haloalkyl, aryl, aralkyl, heteroaryl, heteroaralkyl, cycloalkyl, cycloalkylalkyl, heteroalkyl-substituted cycloalkyl, heterosubstituted cycloalkyl, heteroalkyl, cyanoalkyl, heterocyclyl, heterocyclylalkyl, or —Y$^1$—C(O)—Y$^2$—R$^{11}$ (where Y$^1$ and Y$^2$ are independently either absent or an alkylene group and R$^{11}$ is hydrogen, alkyl, haloalkyl, hydroxy, alkoxy, amino, monoalkylamino or dialkylamino);

R$^3$ is hydrogen, alkyl, cycloalkyl, cycloalkylalkyl, heterosubstituted cycloalkyl, heterocyclyl, aryl, aralkyl, haloalkyl, heteroalkyl, cyanoalkyl, -alkylene-C(=O)—R$^4$ (where R$^4$ is hydrogen, alkyl, hydroxy, alkoxy, amino, monoalkylamino or dialkylamino), or acyl;

Ar$^1$ is aryl;

X$^1$ is O, NR$^5$ or S, where R$^5$ is hydrogen or alkyl; and

X$^2$ is a bond, O, NR$^6$, S or CH$_2$, where R$^6$ is hydrogen or alkyl.

2. The compound according to claim 1 of the formula:

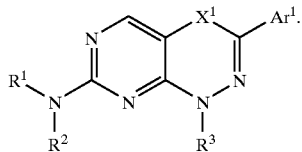

3. The compound according to claim 2, wherein X$^1$ is O.

4. The compound according to claim 3, wherein R$^1$ is hydrogen.

5. The compound according to claim 4, wherein R$^3$ is hydrogen, alkyl, aryl, cycloalkyl, heterocyclyl, heterosubstituted cycloalkyl or heteroalkyl.

6. The compound according to claim 5, wherein R$^3$ is alkyl, heterocyclyl, heterosubstituted cycloalkyl or heteroalkyl.

7. The compound according to claim 4, wherein R$^2$ is heteroalkyl, cycloalkyl, heterocyclyl, heterosubstituted cycloalkyl, heteroaryl or aryl.

8. The compound according to claim 7, wherein R$^2$ is optionally substituted phenyl.

9. The compound according to claim 8, wherein R$^2$ is heterocyclylphenyl, alkylthiophenyl, alkylsulfinylphenyl, alkylsulfonylphenyl, phenyl, halophenyl, hydroxyphenyl, acylphenyl, cyanophenyl, alkoxycarbonylphenyl, carboxamidophenyl, N-alkylcarboxamidophenyl, N,N-dialkylcarboxamidophenyl, alkylsulfonyloxyphenyl, carbamoylphenyl, N-alkylcarbamoylphenyl or N,N-dialkylcarbamoylphenyl.

10. The compound according to claim 9, wherein R$^3$ is alkyl, heterocyclyl, heterosubstituted cycloalkyl or heteroalkyl.

11. The compound according to claim 7, wherein Ar$^1$ is 2-halophenyl, 4-halophenyl, 2,4-dihalophenyl, 2,6-dihalophenyl, 2-alkylphenyl, 1-alkoxyphenyl, 2-alkoxyphenyl, 4-alkoxyphenyl, 3,5-dialkoxyphenyl, 2-halo-5-alkoxyphenyl or 2-dialkylamino-6-fluorophenyl.

12. The compound according to claim 2, wherein R$^1$ is hydrogen.

13. The compound according to claim 12, wherein R$^2$ is heteroalkyl, cycloalkyl, heterocyclyl, heterosubstituted cycloalkyl, heteroaryl or aryl.

14. The compound according to claim 13, wherein R$^3$ is hydrogen, alkyl, aryl, cycloalkyl, heterocyclyl, heterosubstituted cycloalkyl or heteroalkyl.

15. The compound according to claim 14, wherein Ar$^1$ is 2-halophenyl, 4-halophenyl, 2,4-dihalophenyl, 2,6-dihalophenyl, 2-alkylphenyl, 1-alkoxyphenyl, 2-alkoxyphenyl, 4-alkoxyphenyl, 3,5-dialkoxyphenyl, 2-halo-5-alkoxyphenyl or 2-dialkylamino-6-fluorophenyl.

16. The compound according to claim 1, wherein X$^2$ is a bond or CH$_2$.

17. The compound according to claim 16, wherein R$^3$ is hydrogen, alkyl, aryl, cycloalkyl, heterocyclyl, heterosubstituted cycloalkyl or heteroalkyl.

18. The compound according to claim 17, wherein R$^1$ is hydrogen.

19. The compound according to claim 18, wherein R$^2$ is heteroalkyl, heterocyclyl, or heterosubstituted cycloalkyl.

20. The compound according to claim 19, wherein X$^1$ is O.

21. A composition comprising:
(a) a compound of claim 1; and
(b) a pharmaceutically acceptable excipient.

22. A method for treating an FGFR kinase mediated disorder comprising administering to a patient in need of such treatment, an effective amount of a compound of claim 1, wherein said FGFR kinase mediated disorder comprises atherosclerosis.

23. A method for producing a compound of the formula:

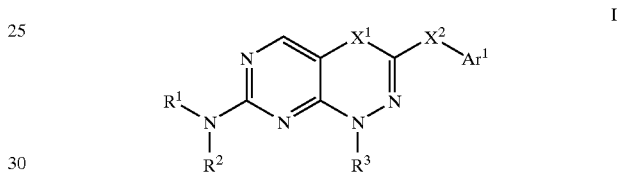

said method comprising the steps of contacting a compound of the formula:

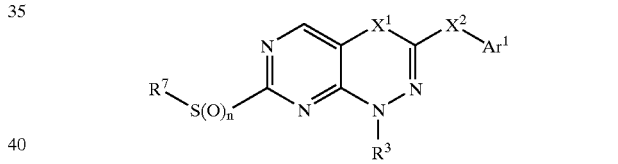

with an amine compound of the formula R$^1$R$^2$NH to produce a compound of Formula. wherein R$^1$ is hydrogen or alkyl;

R$^2$ is alkyl, haloalkyl, aryl, aralkyl, heteroaryl, heteroaralkyl, cycloalkyl, cycloalkylalkyl, heteroalkyl-substituted cycloalkyl, heterosubstituted cycloalkyl, heteroalkyl, cyanoalkyl, heterocyclyl, heterocyclylalkyl or —Y$^1$—C(O)—Y$^2$—R$^{11}$ (where Y$^1$ and Y$^2$ are independently either absent or an alkylene group and R$^{11}$ is hydrogen, alkyl, haloalkyl, hydroxy, alkoxy, amino, monoalkylamino or dialkylamino);

R$^3$ is hydrogen, alkyl, cycloalkyl, cycloalkylalkyl, heterocyclyl, aryl, aralkyl, haloalkyl, heteroalkyl, cyanoalkyl, -alkylene-C(=O)—R$^4$ (where R$^4$ is hydrogen, alkyl, hydroxy, alkoxy, amino, monoalkylamino or dialkylamino) or acyl;

Ar$^1$ is aryl;

X$^1$ is O, NR$^5$ or S, where R$^5$ is hydrogen or alkyl;

X$^2$ is a bond, O, NR$^6$, S or CH$_2$, where R$^6$ is hydrogen or alkyl;

n is an integer from 0 to 2; and

R$^7$ is an alkyl group.

24. The method of claim 23 wherein:

R$^1$ is hydrogen;

R² is heteroalkyl, cycloalkyl, heterocyclyl, heterosubstituted cycloalkyl, heteroaryl or aryl;

R³ is hydrogen, alkyl, aryl, cycloalkyl, heterocyclyl, heterosubstituted cycloalkyl or heteroalkyl;

Ar¹ is aryl;

X¹ is O;

X² is a bond; and n is 1 or 2.

25. The compound of claim 10, wherein R³ is methyl.

26. The compound of claim 25, wherein R² is 4-(morpholin-4-yl)phenyl.

27. The compound of claim 26, wherein Ar¹ is 2-bromophenyl.

28. The compound of claim 26, wherein Ar¹ is 2,6-dichlorophenyl.

29. The compound of claim 25, wherein R² is 3-methylsulfinylphenyl.

30. The compound of claim 29, wherein Ar¹ is 2-bromophenyl.

* * * * *